United States Patent
Meyer et al.

(10) Patent No.: US 10,434,660 B2
(45) Date of Patent: *Oct. 8, 2019

(54) SURGICAL ROBOTIC ARM ADMITTANCE CONTROL

(71) Applicant: Auris Health, Inc., Redwood City, CA (US)

(72) Inventors: Kurt Christopher Meyer, Redwood City, CA (US); Shu-Yun Chung, San Jose, CA (US); Mingyen Ho, Santa Clara, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/011,317

(22) Filed: Jun. 18, 2018

(65) Prior Publication Data

US 2019/0105785 A1    Apr. 11, 2019

Related U.S. Application Data

(63) Continuation of application No. 15/729,558, filed on Oct. 10, 2017, now Pat. No. 10,016,900.

(51) Int. Cl.
  *B25J 13/08*    (2006.01)
  *A61B 17/00*    (2006.01)
  (Continued)

(52) U.S. Cl.
  CPC ............. *B25J 13/085* (2013.01); *A61B 34/30* (2016.02); *A61B 46/10* (2016.02); *B25J 9/0084* (2013.01);
  (Continued)

(58) Field of Classification Search
  CPC ....... B25J 13/085; B25J 9/0084; A61B 34/30; A61B 34/77; A61B 50/13; A61B 90/50;
  (Continued)

(56) References Cited

U.S. PATENT DOCUMENTS

| 4,748,969 A | 6/1988 | Wardle |
| 5,402,801 A | 4/1995 | Taylor |

(Continued)

FOREIGN PATENT DOCUMENTS

| EP | 1 566 150 | 8/2005 |
| EP | 0 830 562 | 7/2009 |

(Continued)

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.

(Continued)

*Primary Examiner* — Robert T Nguyen
(74) *Attorney, Agent, or Firm* — Knobbe, Martens, Olson & Bear, LLP

(57) ABSTRACT

Certain aspects relate to systems and techniques for surgical robotic arm admittance control. In one aspect, there is provided a system including a robotic arm and a processor. The processor may be configured to determine a force at a reference point on the robotic arm based on an output of a torque sensor and receive an indication of a direction of movement of the reference point. The processor may also determine that a component of the force is in the same direction as the direction of movement of the reference point, generate at least one parameter indicative of a target resistance to movement of the robotic arm, and control the motor, based on the at least one parameter, to move the robotic arm in accordance with the target resistance.

30 Claims, 22 Drawing Sheets

(51) Int. Cl.
  *A61B 34/00* (2016.01)
  *A61B 34/30* (2016.01)
  *A61B 50/13* (2016.01)
  *A61B 90/00* (2016.01)
  *A61B 90/50* (2016.01)
  *A61G 13/04* (2006.01)
  *A61B 46/10* (2016.01)
  *B25J 9/00* (2006.01)
  *G05B 19/00* (2006.01)

(52) U.S. Cl.
  CPC .............. *G05B 19/00* (2013.01); *A61B 34/77* (2016.02); *A61B 50/13* (2016.02); *A61B 90/50* (2016.02); *A61B 2017/00477* (2013.01); *A61B 2017/00725* (2013.01); *A61B 2034/301* (2016.02); *A61B 2090/066* (2016.02); *A61B 2090/067* (2016.02); *A61G 13/04* (2013.01)

(58) Field of Classification Search
  CPC .... A61B 2034/301; A61B 2017/00725; A61B 2090/066; A61B 2090/067; A61B 2017/00477; A61B 46/10; A61G 13/04; G05B 19/00
  See application file for complete search history.

(56) References Cited

U.S. PATENT DOCUMENTS

| | | | |
|---|---|---|---|
| 5,408,263 A | 4/1995 | Kikuchi | |
| 5,746,720 A | 5/1998 | Stouder | |
| 6,198,974 B1 | 3/2001 | Webster, Jr. | |
| 6,279,579 B1 | 8/2001 | Riaziat | |
| 6,459,926 B1 | 10/2002 | Nowlin | |
| 6,522,906 B1 | 2/2003 | Salisbury et al. | |
| 6,837,846 B2 | 1/2005 | Jaffe | |
| 6,850,817 B1 | 2/2005 | Green | |
| 7,699,855 B2 | 4/2010 | Anderson | |
| 8,469,947 B2 | 6/2013 | Devengenzo | |
| 8,506,555 B2 | 8/2013 | Ruiz Morales | |
| 8,945,095 B2 | 2/2015 | Blumenkranz | |
| 9,226,796 B2 | 1/2016 | Bowling | |
| 9,289,578 B2 | 3/2016 | Walker et al. | |
| 9,314,306 B2 | 4/2016 | Yu | |
| 9,480,534 B2 | 11/2016 | Bowling | |
| 9,504,604 B2 | 11/2016 | Alvarez | |
| 9,561,083 B2 | 2/2017 | Yu et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,795,445 B2 | 10/2017 | Bowling | |
| 9,818,681 B2 | 11/2017 | Machida | |
| 9,820,818 B2 | 11/2017 | Malackowski | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,004,562 B2 | 6/2018 | Kostrzewski | |
| 10,004,569 B2 | 6/2018 | Singh | |
| 10,016,900 B1* | 7/2018 | Meyer .................. | A61B 46/10 |
| 10,022,192 B1 | 7/2018 | Ummalaneni | |
| 10,154,829 B2* | 12/2018 | Henderson .......... | A61B 8/4427 |
| 2002/0193685 A1 | 12/2002 | Mate | |
| 2003/0045778 A1 | 3/2003 | Ohline | |
| 2003/0182091 A1 | 9/2003 | Kukuk | |
| 2004/0257021 A1 | 12/2004 | Chang et al. | |
| 2005/0043718 A1 | 2/2005 | Madhani | |
| 2005/0065400 A1 | 3/2005 | Banik | |
| 2005/0256398 A1 | 11/2005 | Hastings | |
| 2005/0261551 A1 | 11/2005 | Couvillon | |
| 2006/0015096 A1 | 1/2006 | Hauck et al. | |
| 2006/0412931 | 2/2006 | Mehdizadeh | |
| 2006/0079756 A1 | 4/2006 | Lloyd et al. | |
| 2007/0013336 A1 | 1/2007 | Nowlin et al. | |
| 2007/0043455 A1 | 2/2007 | Viswanathan | |
| 2007/0135886 A1 | 6/2007 | Maschke | |
| 2007/0144298 A1 | 6/2007 | Miller | |
| 2007/0150155 A1 | 6/2007 | Kawai | |
| 2007/0253599 A1 | 11/2007 | White et al. | |
| 2007/0287992 A1 | 12/2007 | Diolaiti | |
| 2008/0231221 A1 | 9/2008 | Ogawa | |
| 2008/0255505 A1 | 10/2008 | Carlson et al. | |
| 2009/0076534 A1 | 3/2009 | Shelton | |
| 2009/0099445 A1 | 4/2009 | Burger | |
| 2009/0088634 A1 | 5/2009 | Zhao | |
| 2009/0245600 A1 | 10/2009 | Hoffman | |
| 2009/0248037 A1 | 10/2009 | Prisco | |
| 2009/0259412 A1* | 10/2009 | Brogardh ............... | B25J 9/1633 |
| | | | 702/41 |
| 2009/0287354 A1 | 11/2009 | Choi | |
| 2010/0030115 A1 | 2/2010 | Fujimoto | |
| 2010/0076263 A1 | 3/2010 | Tanaka | |
| 2010/0121138 A1 | 5/2010 | Goldenberg et al. | |
| 2010/0234999 A1 | 9/2010 | Nakajima | |
| 2010/0256812 A1 | 10/2010 | Tsusaka et al. | |
| 2011/0040411 A1* | 2/2011 | Murayama ................ | B25J 5/02 |
| | | | 700/260 |
| 2011/0082462 A1 | 4/2011 | Suarez | |
| 2011/0137122 A1 | 6/2011 | Kawai | |
| 2011/0144479 A1 | 6/2011 | Hastings et al. | |
| 2011/0153252 A1 | 6/2011 | Govari | |
| 2011/0160570 A1 | 6/2011 | Kariv | |
| 2011/0208355 A1* | 8/2011 | Tsusaka ................ | B25J 9/1664 |
| | | | 700/246 |
| 2011/0319910 A1 | 12/2011 | Roelle et al. | |
| 2012/0046522 A1 | 2/2012 | Naito | |
| 2012/0046542 A1 | 2/2012 | Csavoy et al. | |
| 2012/0071752 A1 | 3/2012 | Sewell | |
| 2012/0123441 A1 | 5/2012 | Au | |
| 2012/0209293 A1 | 8/2012 | Carlson | |
| 2012/0253276 A1 | 10/2012 | Govari et al. | |
| 2013/0041509 A1 | 2/2013 | Saito | |
| 2013/0090530 A1 | 4/2013 | Ramamurthy | |
| 2013/0102846 A1 | 4/2013 | Sjostrom | |
| 2013/0165945 A9 | 6/2013 | Roelle | |
| 2013/0173058 A1* | 7/2013 | Seo ........................ | G05B 15/00 |
| | | | 700/260 |
| 2013/0325030 A1 | 12/2013 | Hourtash et al. | |
| 2014/0052154 A1 | 2/2014 | Griffiths | |
| 2014/0114180 A1 | 4/2014 | Jain | |
| 2014/0135985 A1 | 5/2014 | Coste-Maniere et al. | |
| 2014/0142591 A1 | 5/2014 | Alvarez et al. | |
| 2014/0163664 A1 | 6/2014 | Goldsmith | |
| 2014/0222207 A1 | 8/2014 | Bowling et al. | |
| 2014/0296870 A1 | 10/2014 | Stern et al. | |
| 2014/0309649 A1 | 10/2014 | Alvarez et al. | |
| 2014/0357984 A1 | 12/2014 | Wallace et al. | |
| 2014/0364870 A1 | 12/2014 | Alvarez et al. | |
| 2014/0379000 A1 | 12/2014 | Romo et al. | |
| 2015/0051592 A1 | 2/2015 | Kintz | |
| 2015/0051732 A1* | 2/2015 | Grygorowicz ............. | B25J 1/02 |
| | | | 700/257 |
| 2015/0066051 A1* | 3/2015 | Kwon ....................... | B25J 3/04 |
| | | | 606/130 |
| 2015/0088161 A1 | 3/2015 | Hata | |
| 2015/0101442 A1 | 4/2015 | Romo | |
| 2015/0104284 A1 | 4/2015 | Riedel | |
| 2015/0119638 A1 | 4/2015 | Yu et al. | |
| 2015/0164594 A1 | 6/2015 | Romo et al. | |
| 2015/0164596 A1 | 6/2015 | Romo | |
| 2015/0202015 A1 | 7/2015 | Elhawary | |
| 2015/0248121 A1 | 9/2015 | Nilsson | |
| 2015/0265359 A1 | 9/2015 | Camarillo | |

(56) References Cited

U.S. PATENT DOCUMENTS

| | | | |
|---|---|---|---|
| 2015/0297864 A1 | 10/2015 | Kokish et al. | |
| 2015/0323398 A1* | 11/2015 | Lauzier | B25J 9/0081 73/862.08 |
| 2015/0328771 A1* | 11/2015 | Yuelai | B25J 9/1612 414/730 |
| 2015/0335480 A1 | 11/2015 | Alvarez et al. | |
| 2015/0342695 A1 | 12/2015 | He | |
| 2015/0359597 A1 | 12/2015 | Gombert et al. | |
| 2015/0374446 A1 | 12/2015 | Malackowski | |
| 2016/0001038 A1 | 1/2016 | Romo et al. | |
| 2016/0016319 A1 | 1/2016 | Remirez | |
| 2016/0081568 A1 | 3/2016 | Kolberg | |
| 2016/0100772 A1 | 4/2016 | Ikuma | |
| 2016/0100896 A1 | 4/2016 | Yu | |
| 2016/0144509 A1* | 5/2016 | Gulhar | B25J 9/1653 700/253 |
| 2016/0158601 A1* | 6/2016 | Lee | A63B 24/0062 482/8 |
| 2016/0184032 A1* | 6/2016 | Romo | A61B 10/04 606/130 |
| 2016/0022189 A1 | 8/2016 | Nilsson et al. | |
| 2016/0221189 A1 | 8/2016 | Nilsson | |
| 2016/0270865 A1 | 9/2016 | Landey et al. | |
| 2016/0279405 A1 | 9/2016 | Riley | |
| 2016/0287279 A1 | 10/2016 | Bovay et al. | |
| 2016/0296294 A1 | 10/2016 | Moll et al. | |
| 2016/0338787 A1 | 11/2016 | Popovic | |
| 2016/0346924 A1 | 12/2016 | Hasegawa | |
| 2016/0354925 A1 | 12/2016 | Shimodaira | |
| 2016/0374541 A1 | 12/2016 | Agrawal et al. | |
| 2017/0007336 A1 | 1/2017 | Tsuboi | |
| 2017/0007337 A1 | 1/2017 | Dan | |
| 2017/0007342 A1 | 1/2017 | Kasai | |
| 2017/0100199 A1 | 4/2017 | Yu et al. | |
| 2017/0119413 A1 | 5/2017 | Romo | |
| 2017/0119481 A1 | 5/2017 | Romo et al. | |
| 2017/0151027 A1 | 6/2017 | Walker et al. | |
| 2017/0165011 A1 | 6/2017 | Bovay et al. | |
| 2017/0165834 A1 | 6/2017 | Hares | |
| 2017/0172673 A1 | 6/2017 | Yu et al. | |
| 2017/0172680 A1 | 6/2017 | Bowling | |
| 2017/0202627 A1 | 7/2017 | Sramek et al. | |
| 2017/0209073 A1 | 7/2017 | Sramek et al. | |
| 2017/0245955 A1 | 8/2017 | Bowling | |
| 2017/0274530 A1 | 9/2017 | Mottram | |
| 2017/0280978 A1 | 10/2017 | Yamamoto | |
| 2017/0281049 A1 | 10/2017 | Yamamoto | |
| 2017/0290631 A1 | 10/2017 | Lee et al. | |
| 2017/0333679 A1 | 11/2017 | Jiang | |
| 2017/0340396 A1 | 11/2017 | Romo et al. | |
| 2017/0365055 A1 | 12/2017 | Mintz et al. | |
| 2017/0367782 A1 | 12/2017 | Schuh et al. | |
| 2018/0025666 A1 | 1/2018 | Ho et al. | |
| 2018/0177383 A1 | 6/2018 | Noonan et al. | |
| 2018/0177556 A1 | 6/2018 | Noonan et al. | |
| 2018/0177561 A1 | 6/2018 | Mintz et al. | |
| 2018/0214011 A1 | 8/2018 | Graetzel et al. | |
| 2018/0221038 A1 | 8/2018 | Noonan et al. | |
| 2018/0221039 A1 | 8/2018 | Shah | |
| 2018/0250083 A1 | 9/2018 | Schuh et al. | |
| 2018/0271616 A1 | 9/2018 | Schuh et al. | |
| 2018/0279852 A1 | 10/2018 | Rafii-Tari et al. | |
| 2018/0280660 A1 | 10/2018 | Landey et al. | |
| 2018/0289243 A1 | 10/2018 | Landey et al. | |
| 2018/0289431 A1 | 10/2018 | Draper et al. | |

FOREIGN PATENT DOCUMENTS

| | | |
|---|---|---|
| EP | 2 392 435 | 12/2011 |
| WO | WO 01/56457 | 8/2001 |
| WO | WO 06/122061 | 11/2006 |
| WO | WO 09/120940 | 10/2009 |
| WO | WO 11/132409 | 10/2011 |

OTHER PUBLICATIONS

Verdaasdonk et al., Jan. 23, 2013, Effect of microsecond pulse length and tip shape on explosive bubble formation of 2.78 μm Er,Cr;YSGG and 2.94 μm Er:YAG laser, Proceedings of SPIE, vol. 8221, 12.

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

Skarecky et al., 2008, Zero positive surgical margins after radical prostatectomy: is the end in sight?, Expert Review of Medical Devices, 5(6):709-717.

International Search Report and Written Opinion dated Oct. 25, 2018 in application No. PCT/US18/52967.

* cited by examiner

SURGICAL ROBOTIC ARM ADMITTANCE CONTROL

CROSS-REFERENCE TO RELATED APPLICATION

This application is a continuation of application Ser. No. 15/729,558, filed Oct. 10, 2017, which is hereby incorporated by reference in its entirety.

TECHNICAL FIELD

The systems and methods disclosed herein are directed to surgical robotic arm admittance, and more particularly to techniques for controlling the pose of a robotic arm based on forces applied thereto.

BACKGROUND

Medical procedures such as endoscopy (e.g., bronchoscopy) may involve the insertion of a medical tool into a patient's luminal network (e.g., airways) for diagnostic and/or therapeutic purposes. In certain procedures, one or more of robotic arm(s) are aligned with the patient prior to initiating the procedure. Alignment of the robotic arm(s) provides the system with positional information which relates the position of the robotic arm(s) to the patient. The robotic arm(s) may be manually repositioned by a user of the system during alignment of the robotic arm(s) with the patient.

SUMMARY

The systems, methods and devices of this disclosure each have several innovative aspects, no single one of which is solely responsible for the desirable attributes disclosed herein.

In one aspect, there is provided a system comprising (a) a robotic arm comprising: at least two linkages, at least one joint connecting the at least two linkages, at least one torque sensor configured to detect torque between the at least two linkages, and at least one motor configured to adjust the position of the at least two linkages, (b) a processor; and (c) a memory storing computer-executable instructions to cause the processor to: determine a force at a reference point on the robotic arm based on an output of the torque sensor, receive an indication of a direction of movement of the reference point, determine that a component of the force is in the same direction as the direction of movement of the reference point, generate, based on the determination that the component of the force is in the same direction as the direction of movement of the reference point, at least one parameter indicative of a target resistance to movement of the robotic arm, and control the motor, based on the at least one parameter, to move the robotic arm in accordance with the target resistance.

In another aspect, there is provided a non-transitory computer readable storage medium having stored thereon instructions that, when executed, cause at least one computing device to: determine a force at a reference point on a robotic arm comprising a torque sensor based on an output of the torque sensor, the robotic arm further comprising: two linkages, a joint connecting the two linkages, and a motor configured to adjust the position of the two linkages, the torque sensor configured to detect torque between the two linkages; receive an indication of a direction of movement of the reference point; determine that a component of the force is in the same direction as the direction of movement of the reference point; generate, based on the determination that the component of the force is in the same direction as the direction of movement of the reference point, at least one parameter indicative of a target resistance to movement of the robotic arm; and control the motor, based on the at least one parameter, to move the robotic arm in accordance with the target resistance.

In yet another aspect, there is provided a method of positioning a robotic arm, comprising: determining a force at a reference point on the robotic arm comprising a torque sensor based on an output of the torque sensor, the robotic arm further comprising: two linkages, a joint connecting the two linkages, and a motor configured to adjust the position of the two linkages, the torque sensor configured to detect torque between the two linkages; receiving an indication of a direction of movement of the reference point; determining that a component of the force is in the same direction as the direction of movement of the reference point; generating, based on the determination that the component of the force is in the same direction as the direction of movement of the reference point, at least one parameter indicative of a target resistance to movement of the robotic arm; and controlling the motor, based on the at least one parameter, to move the robotic arm in accordance with the target resistance.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroenterology, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
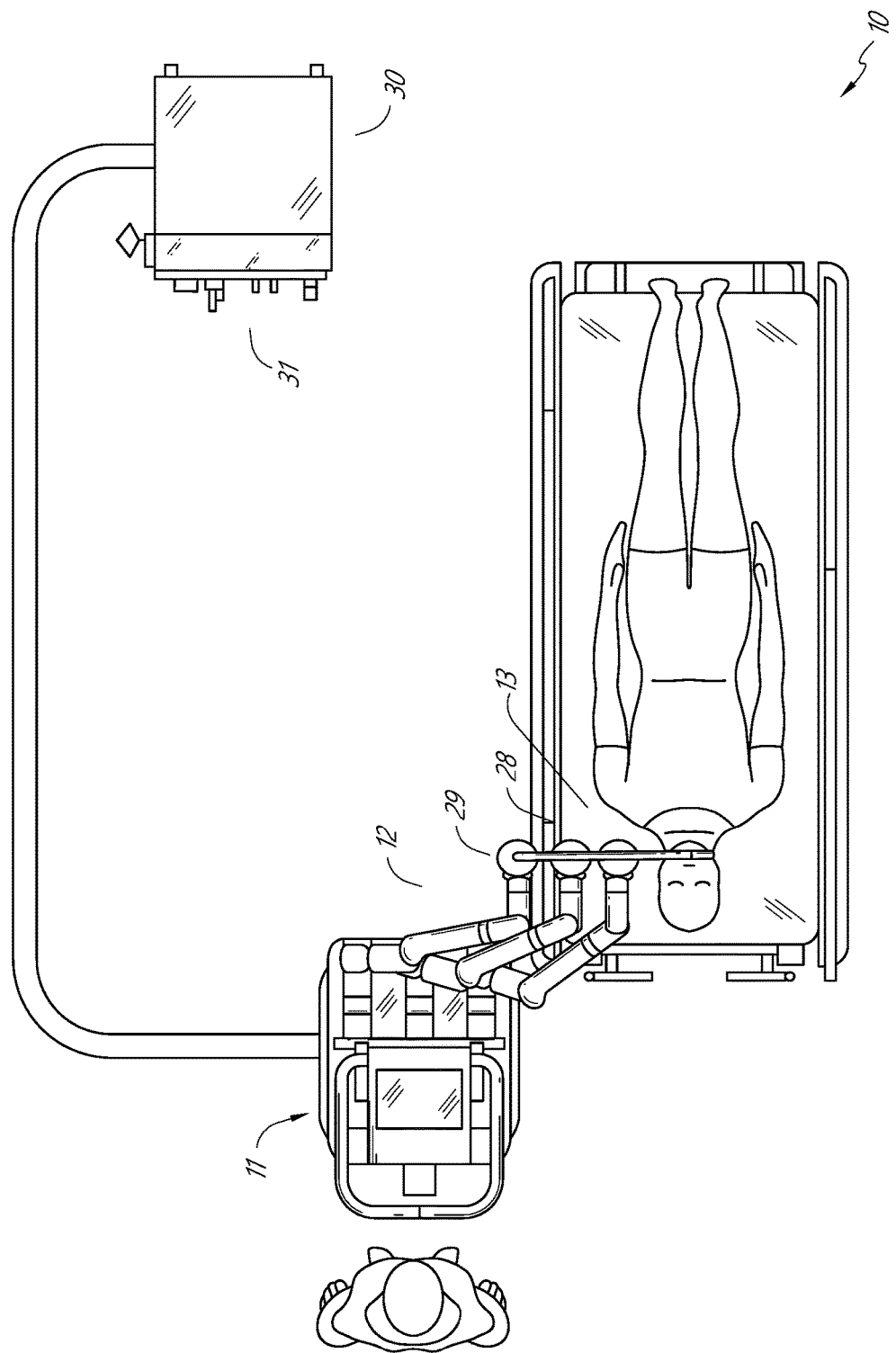
FIG. 1 illustrates an embodiment of a cart-based robotic system arranged for diagnostic and/or therapeutic bronchoscopy procedure(s).
Figure 2:
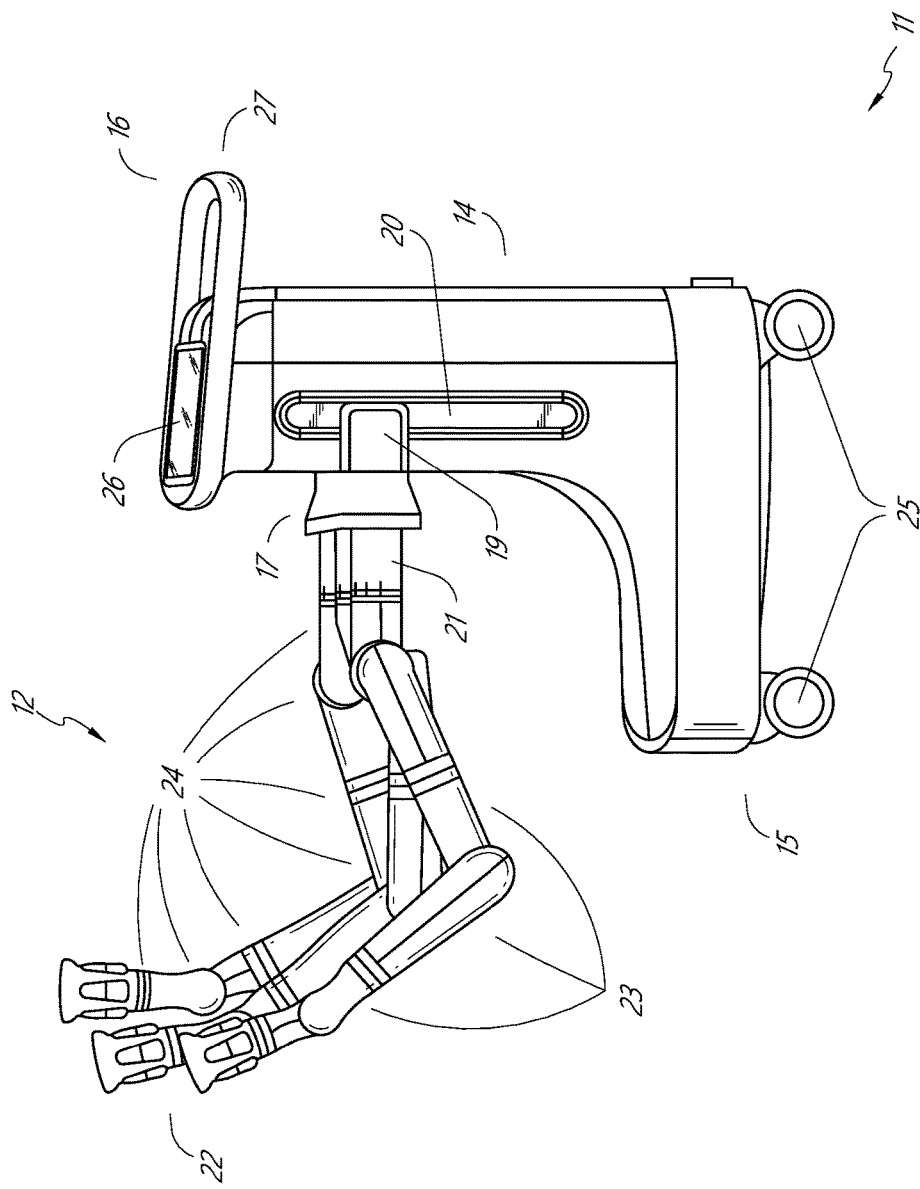
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
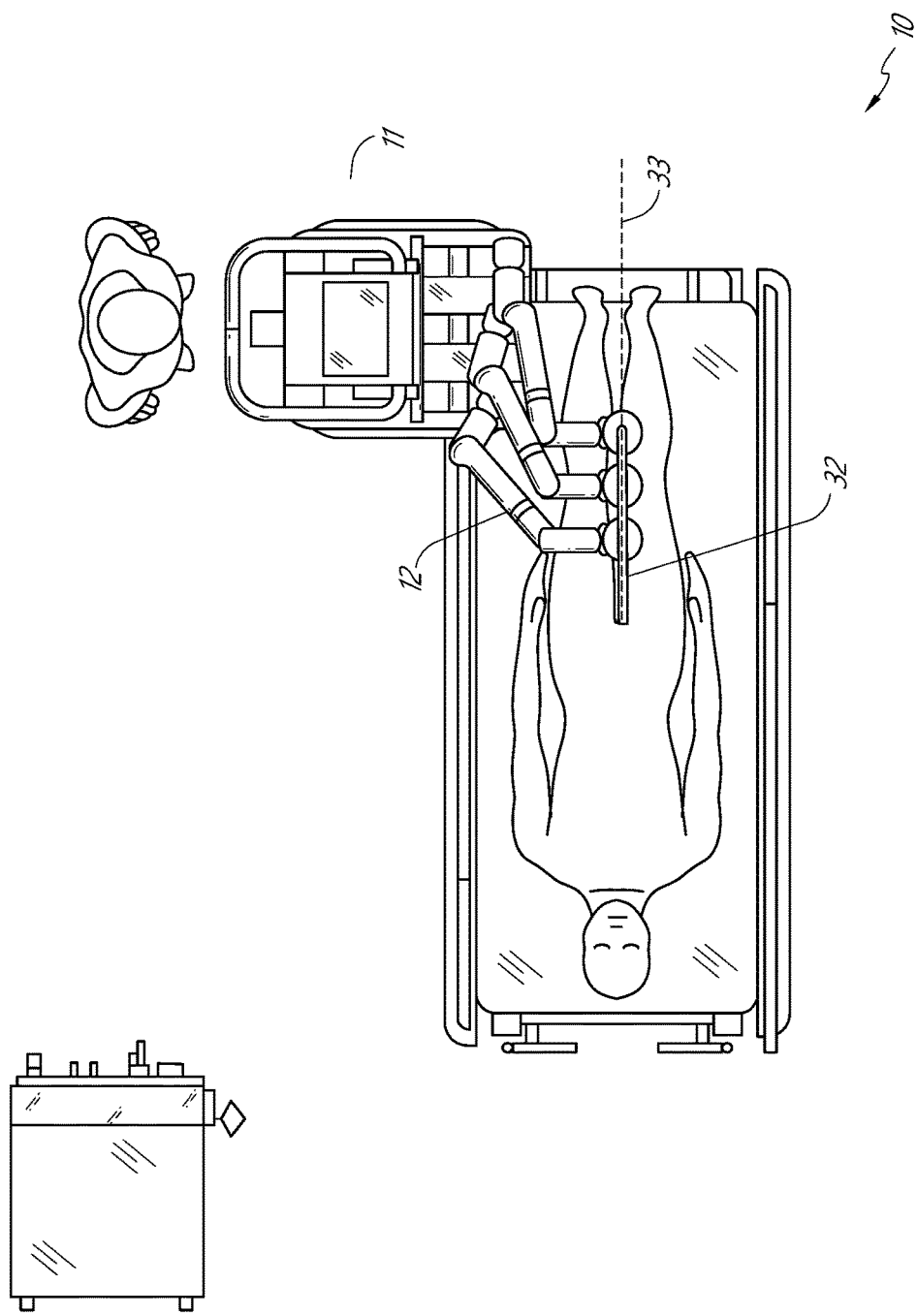
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
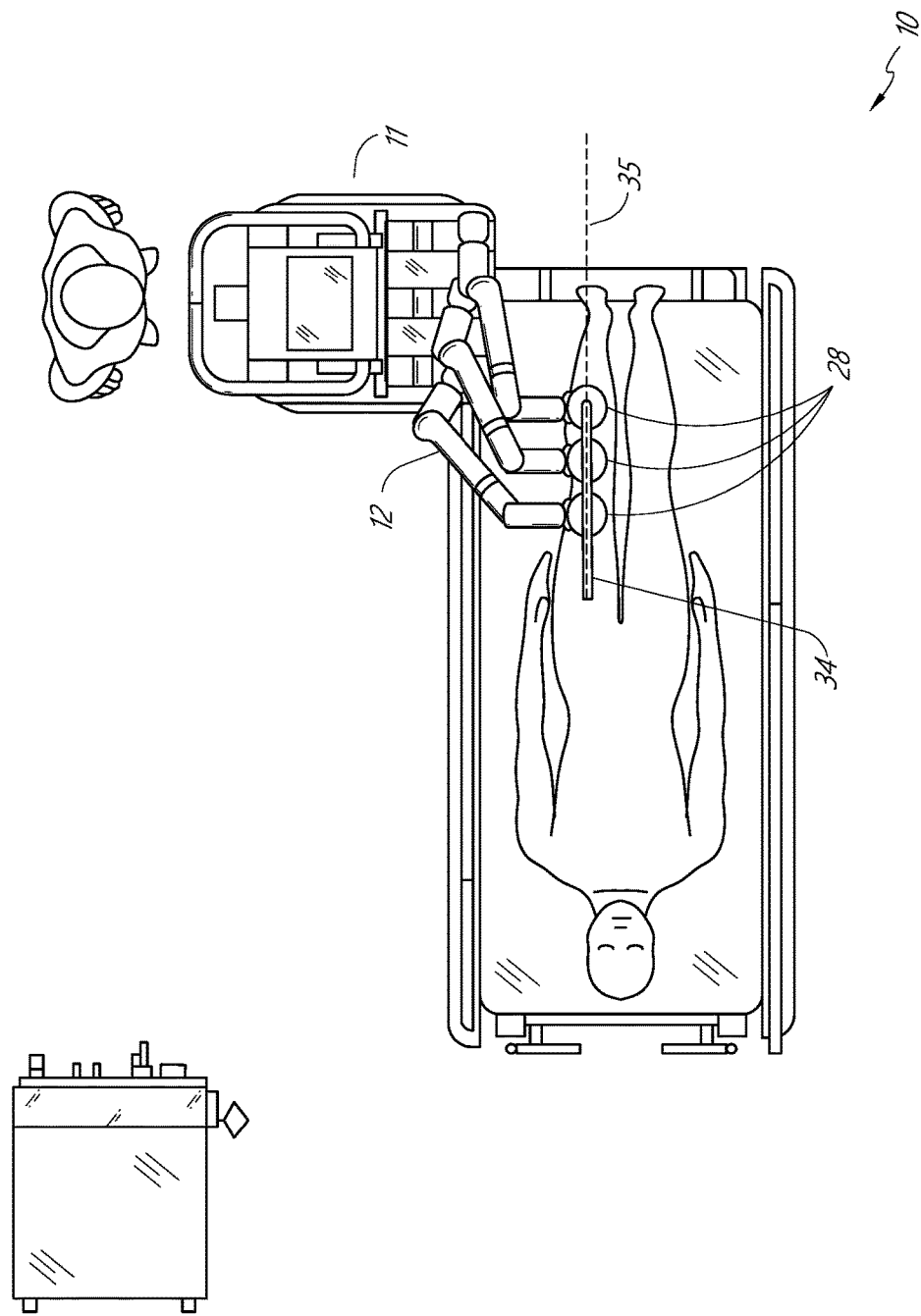
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
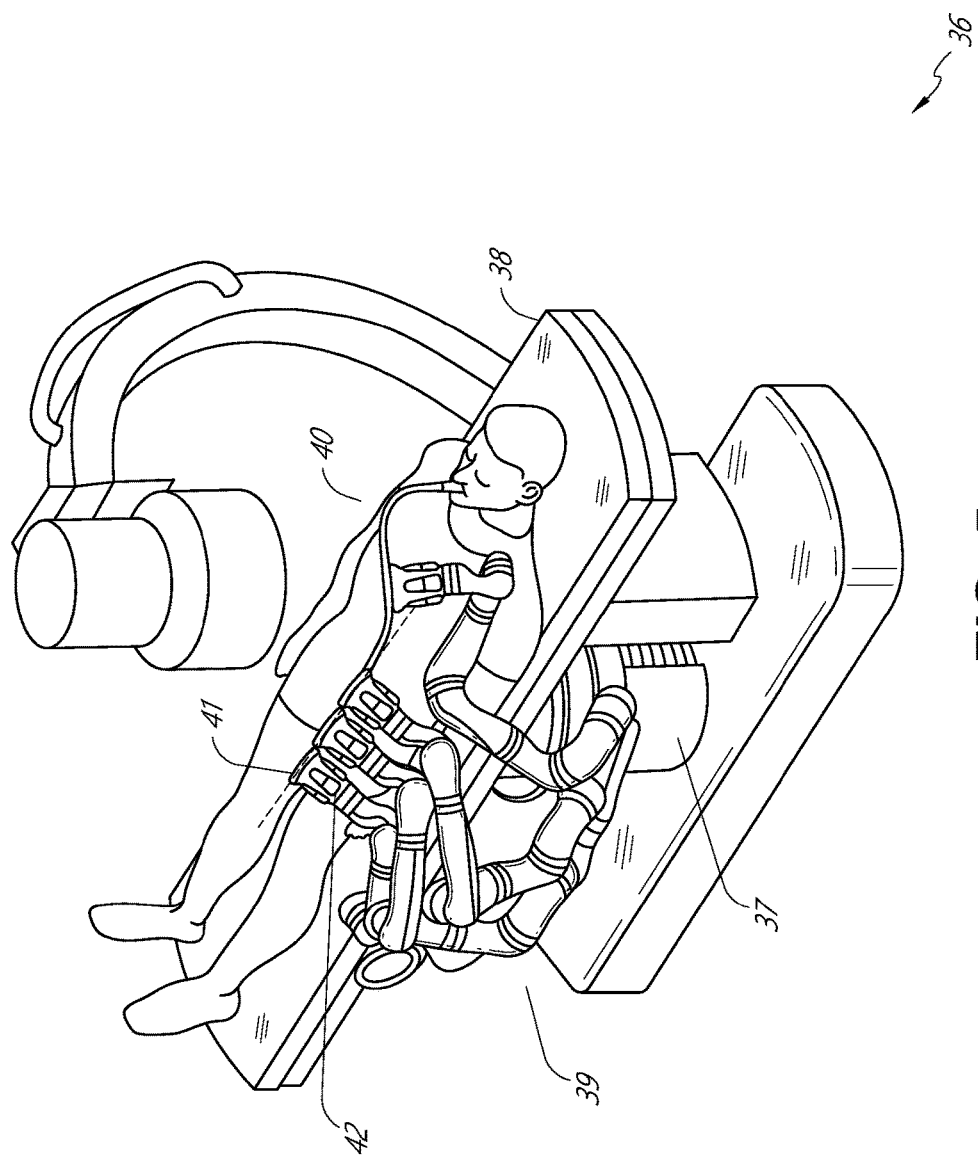
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
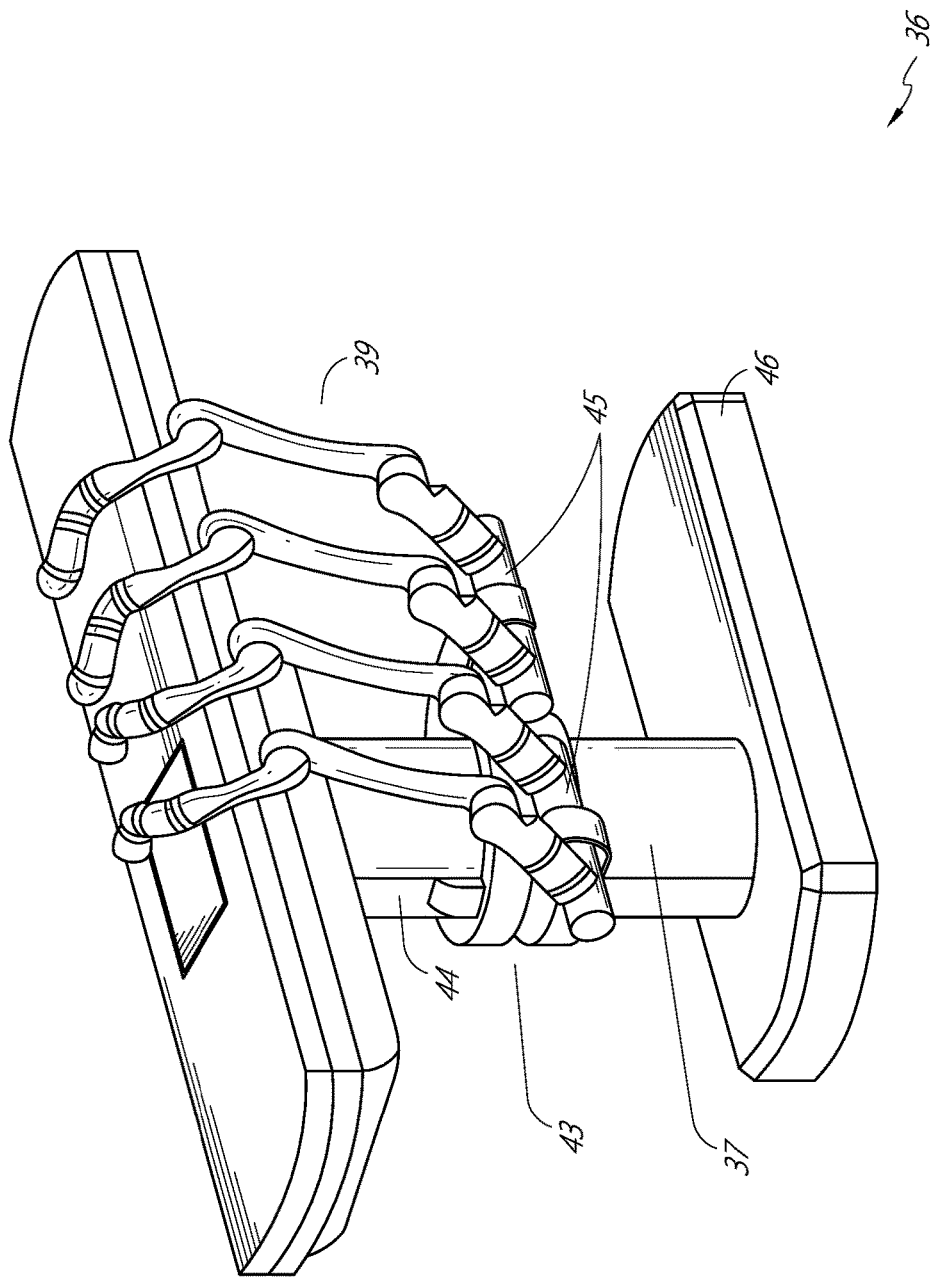
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
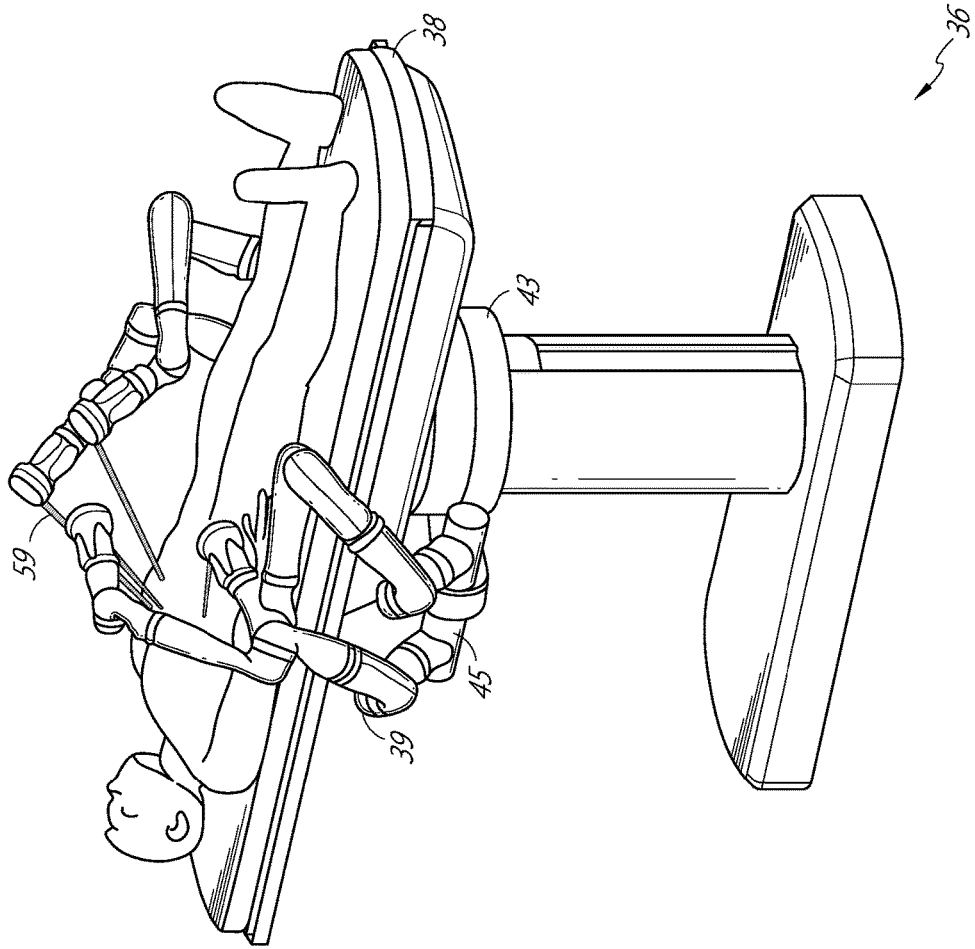
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may be provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
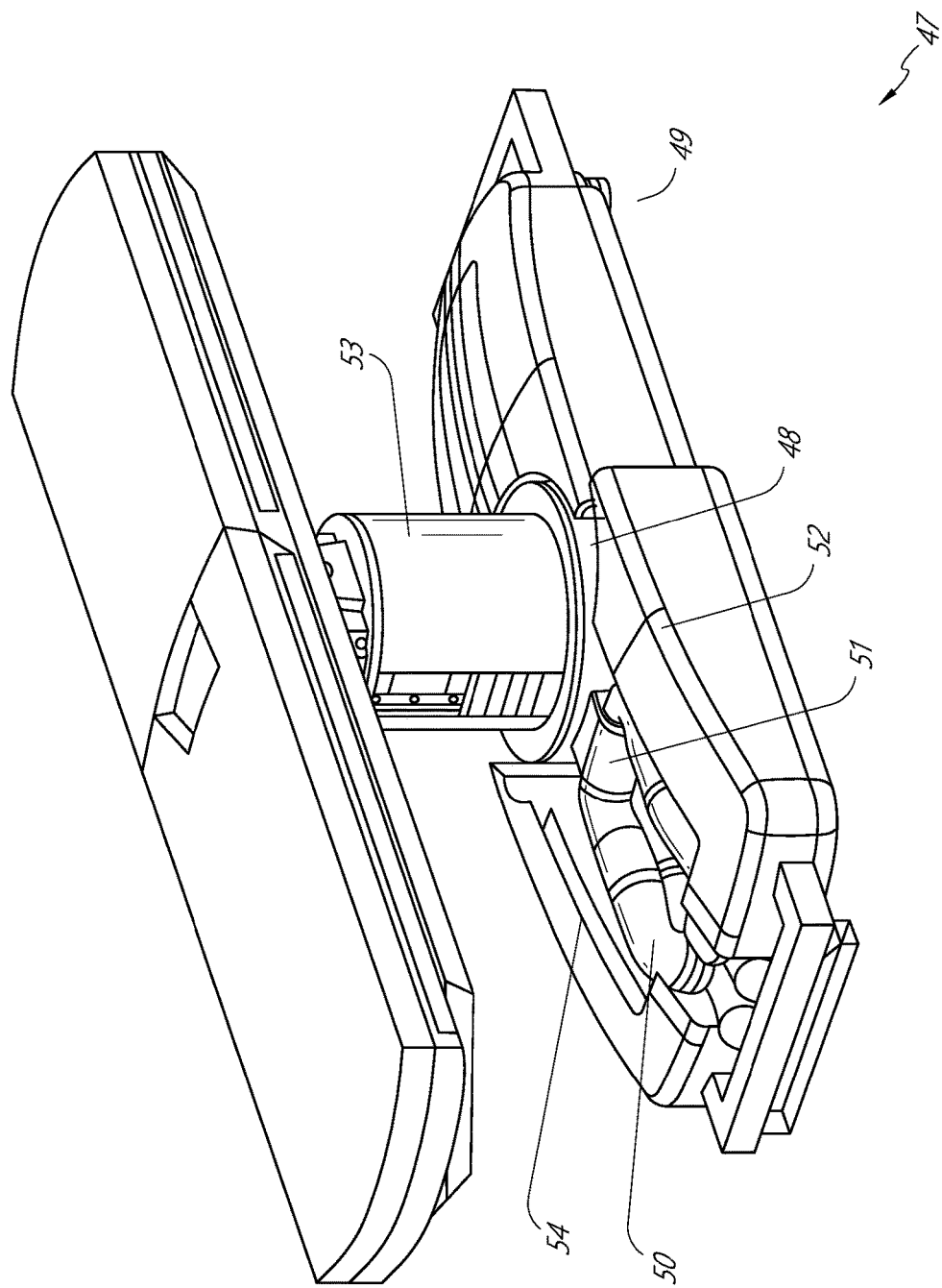
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
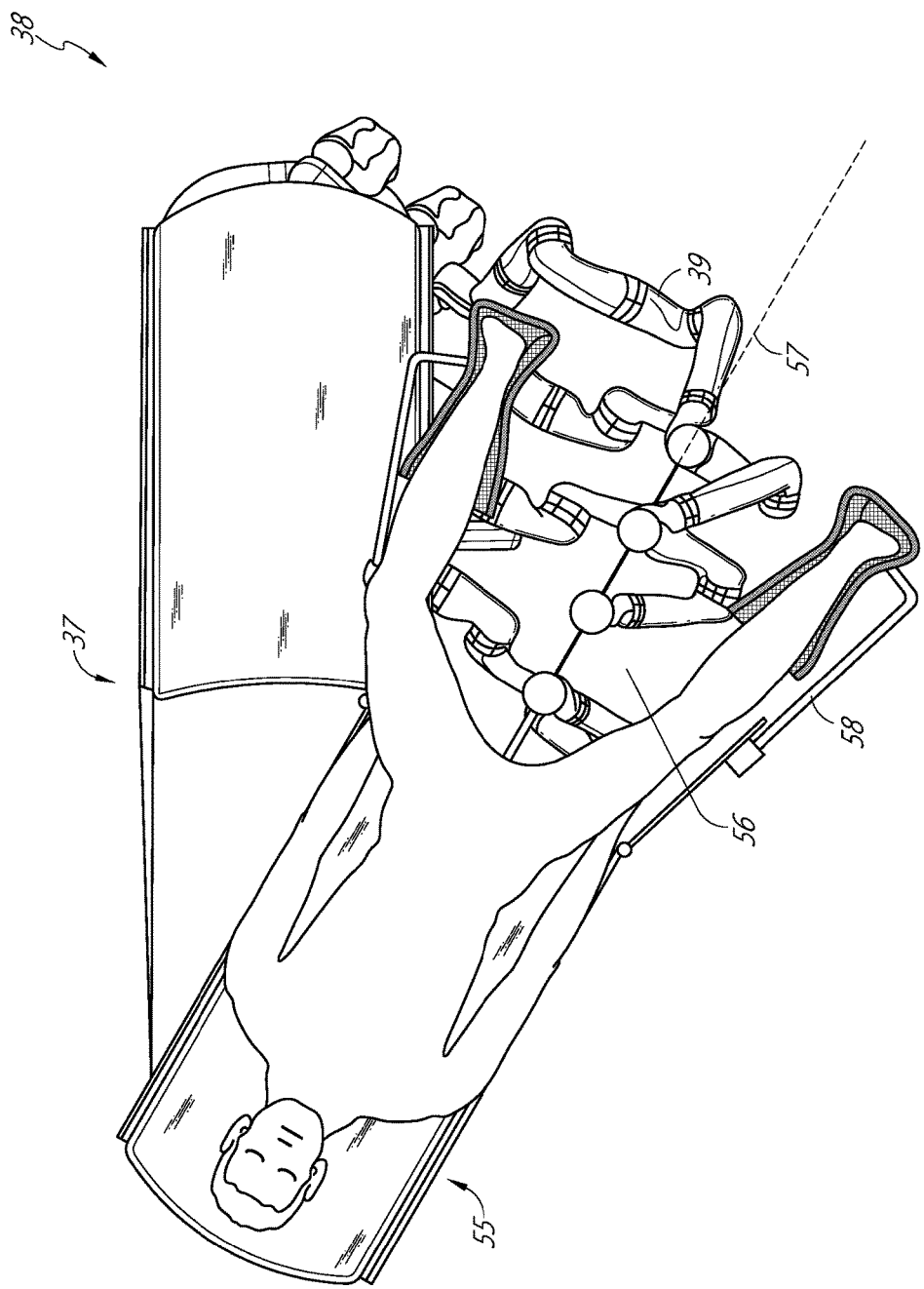
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
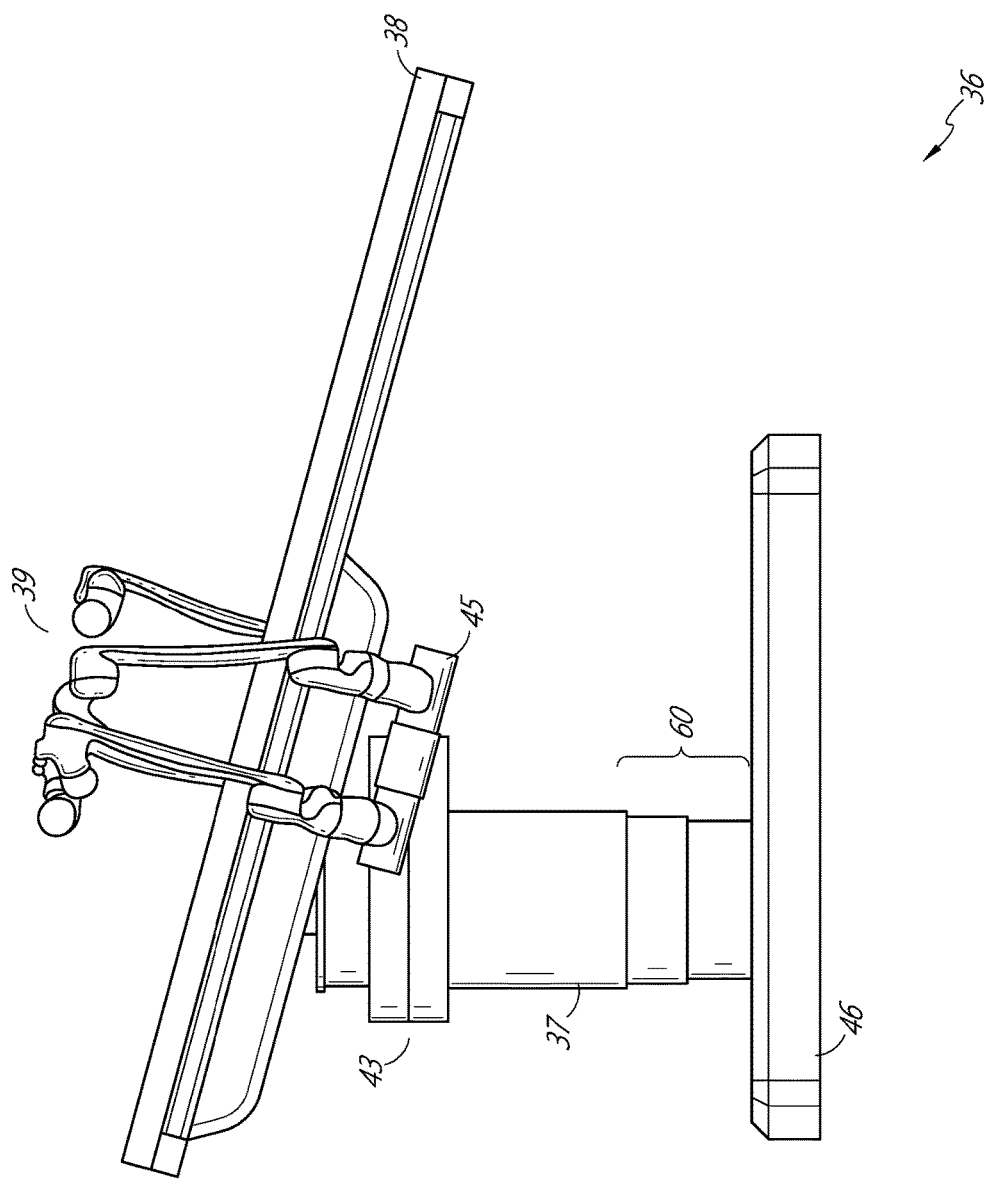
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
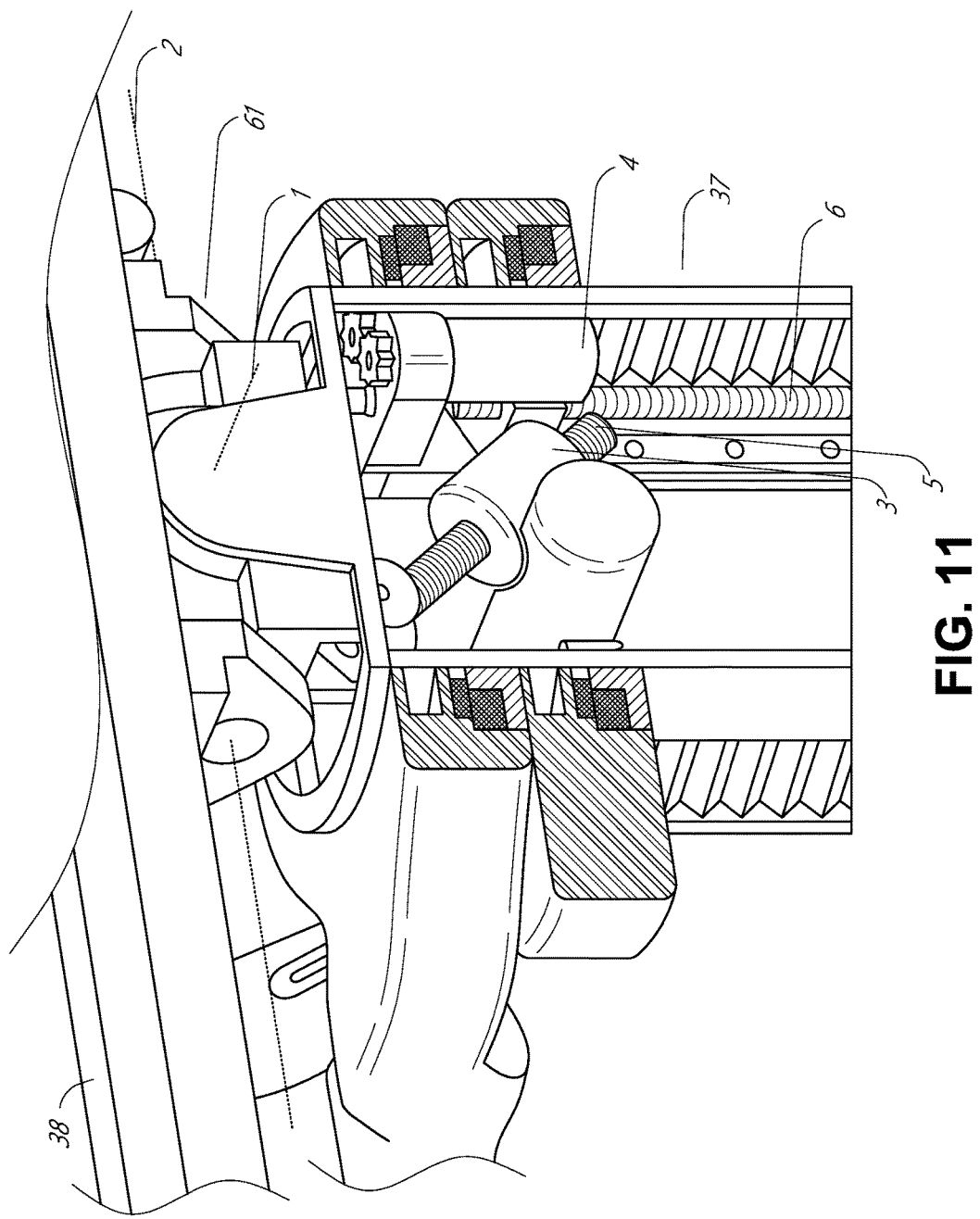
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator" (IDM)) that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
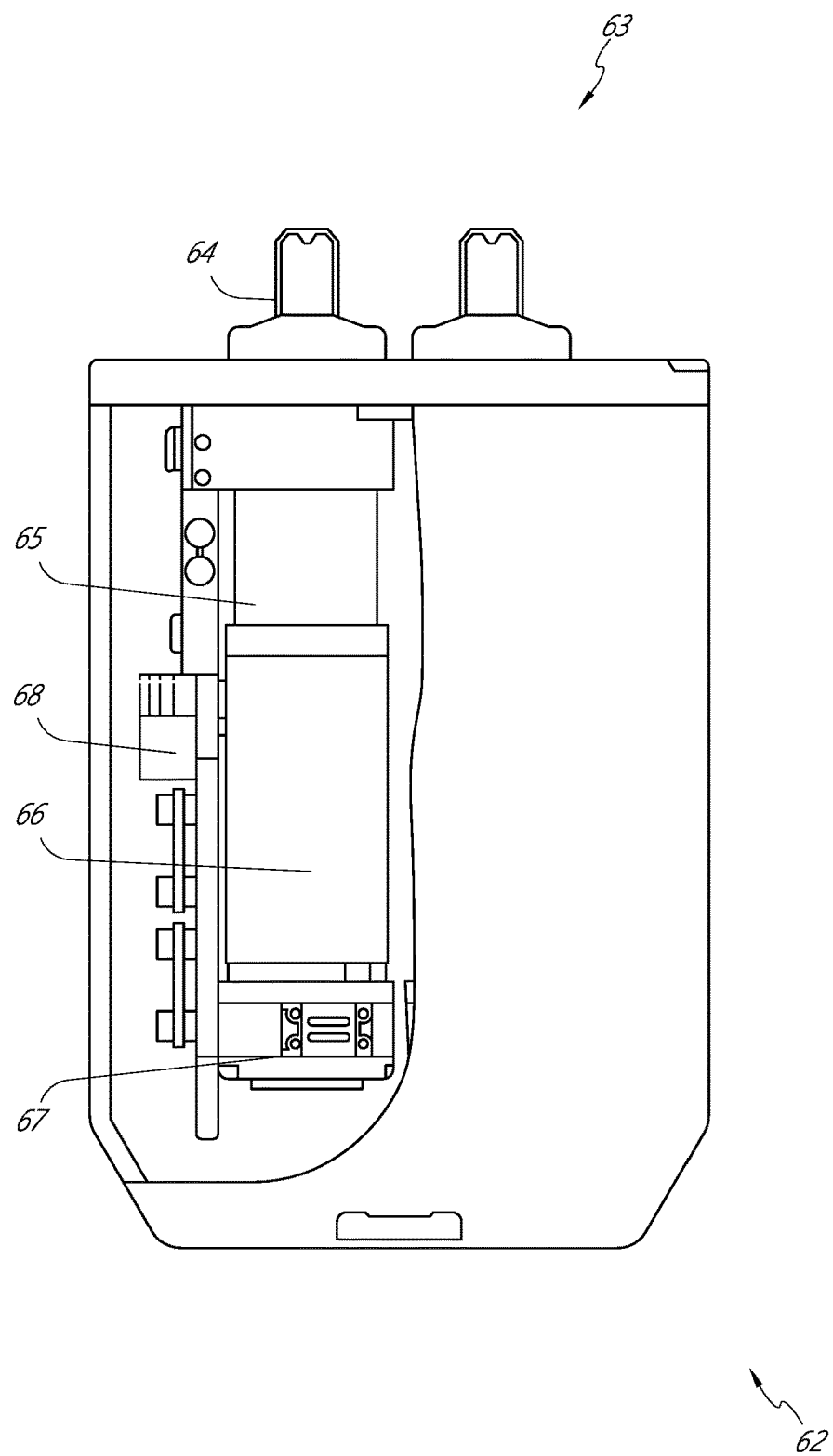
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
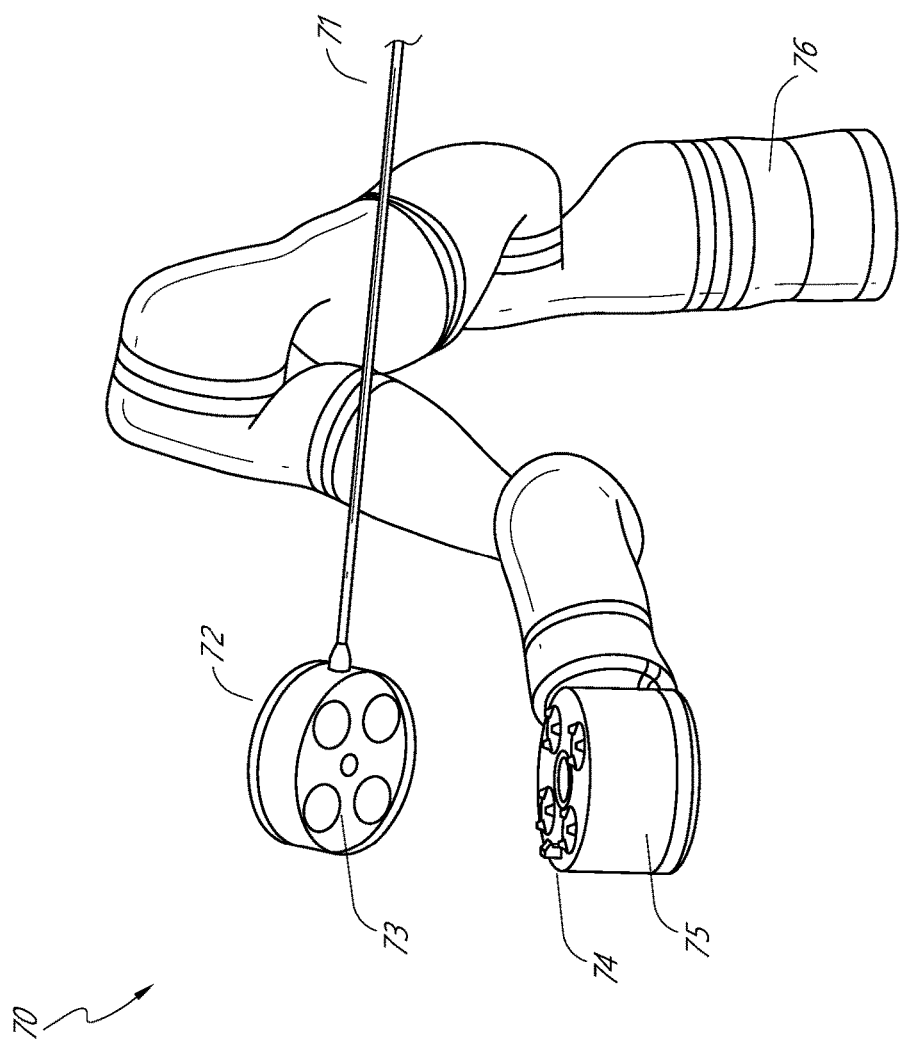
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space.

Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
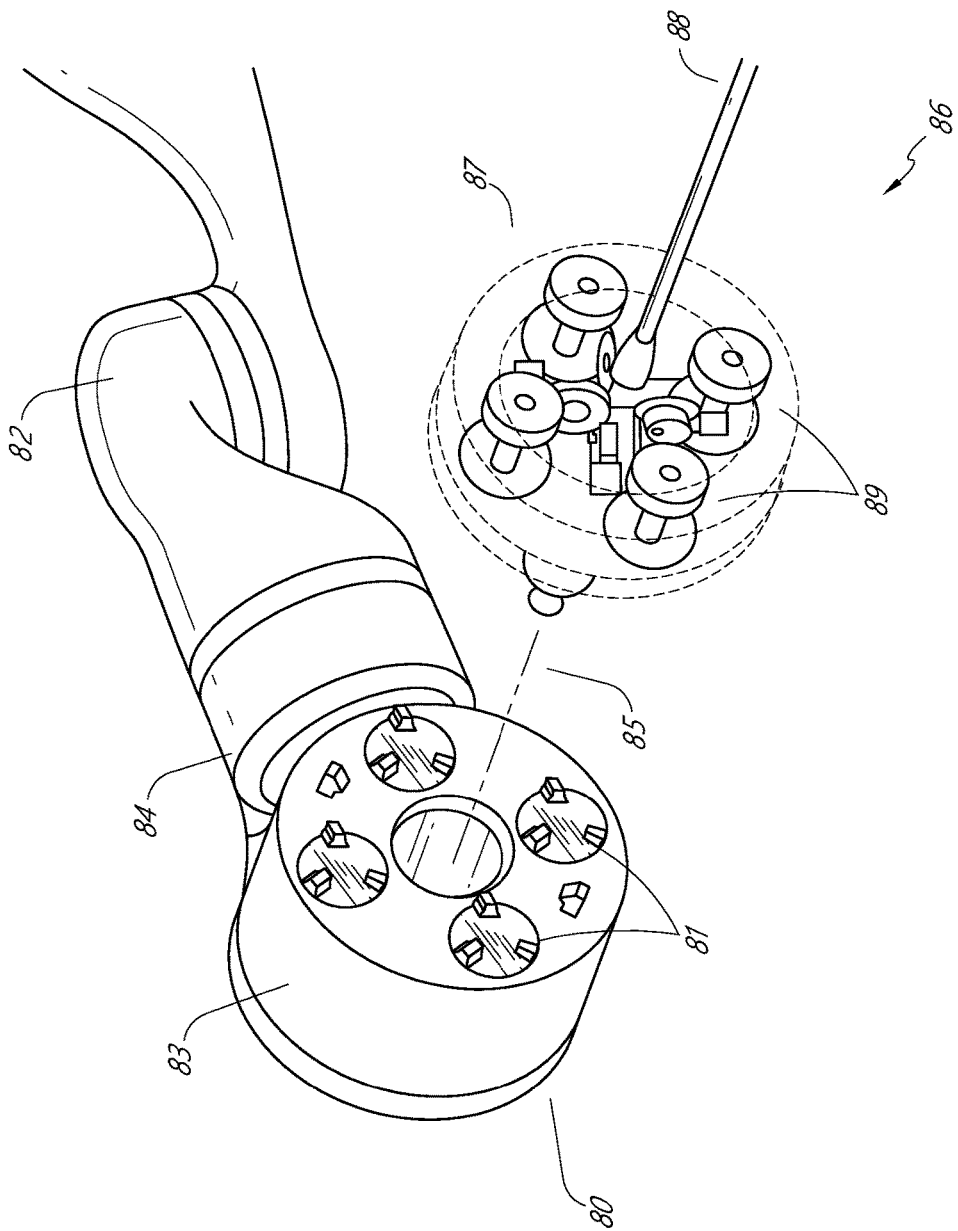
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
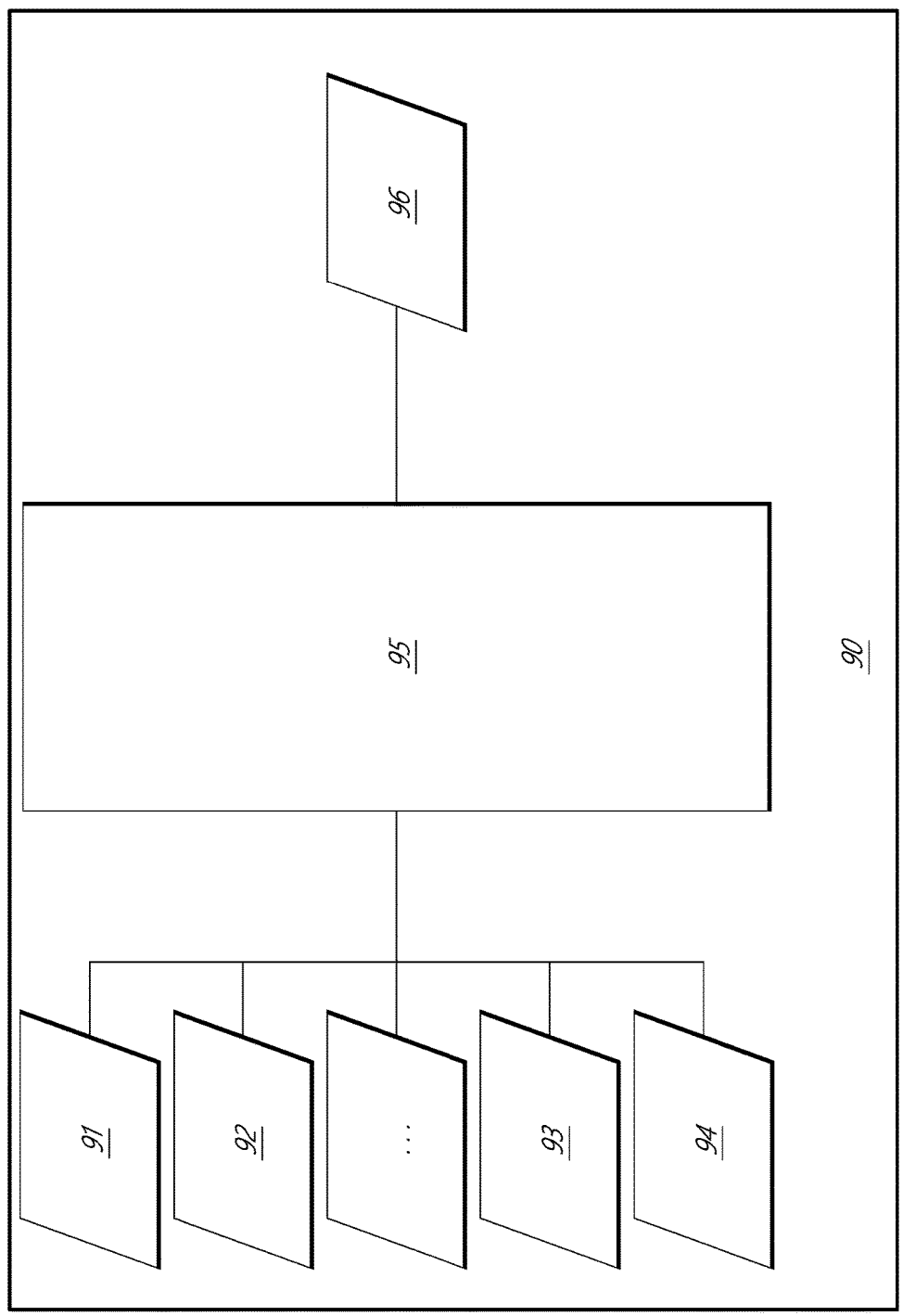
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans generate two-dimensional images, each representing a "slice" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Techniques for Robotic Arm Admittance Control

Embodiments of this disclosure relate to systems and techniques for controlling the movement of one or more robotic arms, for example, based on input received from a user (e.g., a clinician) of a surgical robotic system. There may be circumstances during which the direct control of one or more of the robotic arms of a surgical robotic system (e.g., by applying a force directly to one of the arms) is desirable to a user. For example, the setup of the surgical robotic system for a medical procedure may involve moving at least one robotic arm into a specific pose to be aligned to an alignment device and/or the patient. By grasping the robotic arm and applying a force thereto, the user may be able to directly control the position of the robotic arm in an intuitive manner. As used herein, the term "admittance control mode" (or simply "admittance mode") may refer to a control mode of the surgical robotic system in which the user controls the movement of a robotic arm by applying forces thereto.

The robotic arm may comprise driving components configured to reposition and maintain the current pose of the robotic arm. Thus, in order to provide admittance control functionality, the system may measure the force imparted to the robotic arm by the user and actuate one or more of the driving components using the measured force as an input value.

Without proper interpretation of user input (i.e., force imparted to the robotic arm by the user), the operation and movement of a robotic arm by the drive components may not have a natural or intuitive "feel" to the user (e.g., if the robotic arm accelerates/decelerates in a manner not commensurate with the force that the user applies for the robotic arm). Thus, it may be desirable to control the movement of the robotic arm based on the force applied to the arm by the user in a manner that allows control with a normal to light touch, provides responsive movement, minimizes system lag, provides a sense of control, etc. Additional advantages to the techniques disclosed herein include but are not limited to: providing robotic arm movement (e.g., translation and/or rotation) with a low force-over-time value (e.g., an impulse value less than a threshold value), which can provide both small-scale and large-scale displacement of the robotic arm; providing a robotic arm movement speed that is proportional to the applied force; and terminating movement of the robotic arm promptly when the impulse value reaches zero.

Aspects of this disclosure relate to systems and techniques for measuring user input and controlling the movement of one or more robotic arms to achieve one or more of these advantages.

A. Example System for Admittance Control.

Figure 16:
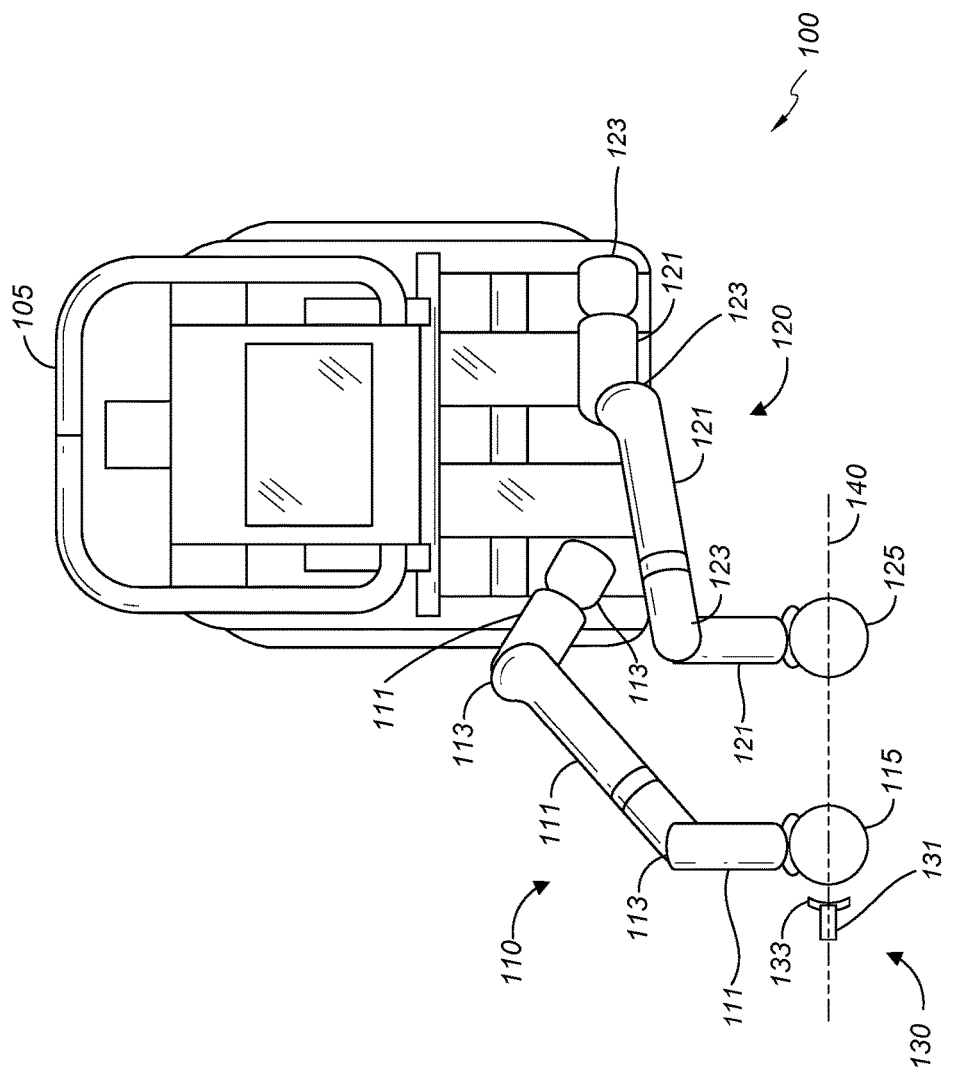
FIG. 16 illustrates an embodiment of a cart-based robotic system configured to control the movement of a robotic arm in an admittance control mode in accordance with aspects of this disclosure.

FIG. 16 illustrates an embodiment of a cart-based robotic system which may be configured to control the movement of a robotic arm in an admittance control mode in accordance with aspects of this disclosure. Although FIG. 16 is directed to an embodiment in which the robotic arm(s) are attached to a cart, this disclosure is not limited thereto, and the techniques described herein are be applicable to, for example, robotic arm(s) attached to a column supporting a patient platform as shown in FIG. 6.

Returning to FIG. 16, provided is a system 100 that may include a cart 105 and one or more robotic arms 110 and 120. The cart 105 may include a processor (not illustrated) and a memory (not illustrated). However, depending on the embodiment, one or more of the processor and the memory may be located on or within another device, such as on the moveable tower 30 illustrated in FIG. 1. Also shown in FIG. 16 is a patient introducer 130 which may be inserted into a patient (not illustrated) prior to a medical procedure. The patient introducer 130 may comprise an introducer tube 131 configured to guide a steerable instrument (not illustrated) into the patient for the medical procedure. The patient introducer may 130 also comprise an alignment member 133 configured to facilitate alignment between the patient introducer 130 and one of the robotic arms 110 and 120.

The robotic arms 110 and 120 may include a first robotic arm 110 and a second robotic arm 120, respectively. However, aspects of this disclosure are also applicable to systems having a greater or fewer number of robotic arms. In the embodiment of FIG. 16, the first robotic arm 110 includes a plurality of linkages 111, a plurality of joints 113, and an IDM 115. Each of the joints 113 connects two adjacent linkages 111. Although not illustrated, the first robotic arm 110 may also include a torque sensor configured to detect torque between two of the linkages 111. In certain implementations, a given joint 113 may house a corresponding torque sensor configured to detect torque between the two linkages 111 adjacent to the given joint 113. Thus, the torque sensor may be located in the joint 113 and may be coupled to the two adjacent linkages 111. A torque sensor may also be provided in the joint 113 that connects the first robotic arm 110 to the cart 105. In certain implementations, the torque sensor(s) may be implemented via a plurality of strain gauges configured to minimize the effects of torques that are not along the axis of rotation of the corresponding joint 113 from affecting the output of the torque sensor.

Additionally, a motor (not illustrated) may be located in each of the joints 113 and may be coupled to the two adjacent linkages 111. Thus, a given joint 113 may further house the motor, which is configured to apply a force between the two adjacent linkages 111 (or between a linkage 111 and the cart 105) in order to adjust the positioning of the two adjacent linkages 111. The IDM 115 may be connected to a distal end of the robotic arm 110. By actuating the motor in one or more of the joints 113 of the first robotic arm 110, the motors may be operable to adjust the posture or pose of the first robotic arm 110, and thus the IDM 115 (e.g., by adjusting the position and/or orientation of one or more joints 113 of the first robotic arm 110) and thereby control a steerable instrument attached to the IDM 115.

Each of the joints 113 may further house a position sensor configured to measure the relative position of the two adjacent linkages 111. Thus, a given joint 113 may further house the position sensor, which may be configured to measure the angle between the two adjacent linkages 111. The system may be able to determine the position of each of the linkages 111 in the first robotic arm 110 based on the output of each of the position sensors. Additionally, as discussed below, the output of the position sensors may be used to determine a force applied to a reference point on the first robotic arm 110. In certain embodiments, a given position sensor may include an encoder. The encoder may be configured to measure the speed and/or position of the motor shaft by reading, for example, coded visual information printed on the motor shaft and may provide feedback to the system representative of the speed and/or position of the motor.

Similar to the first robotic arm 110, the second robotic arm 120 may include a plurality of linkages 121, a plurality of joints 123 connecting adjacent linkages 121, and an IDM 125. Each of the joints 123 may house a corresponding torque sensor, motor, and position sensor (not illustrated). The IDM 125 may also be attached to the steerable instrument to operate the steerable instrument.

In certain embodiments, rather than including separate torque sensor and motor in each of the joints 113 and 123, the motors may also function as torque sensors. For example, when a force is applied to the first robotic arm 110 (e.g., the force of gravity, the force of a collision, a force exerted by a user, etc.), the motor(s) may be configured to apply opposite and opposing force(s) to the joint 113 to maintain the position of the first robotic arm 110. The motor current required in the motor(s) to maintain the first robotic arm 110 position may correspond to the torque applied to the corresponding joints 113.

B. Robotic Arm Setup.

Positioning of one or more of the robotic arms may be one part of a setup procedure for preparing the surgical robotic system for a medical procedure. The specific setup procedure used may depend on the medical procedure being performed, the configuration of the robotic system (e.g., whether the arms are attached to a cart (see FIG. 16) or attached to a column supporting the platform (see FIG. 6)), etc.

Figure 17:
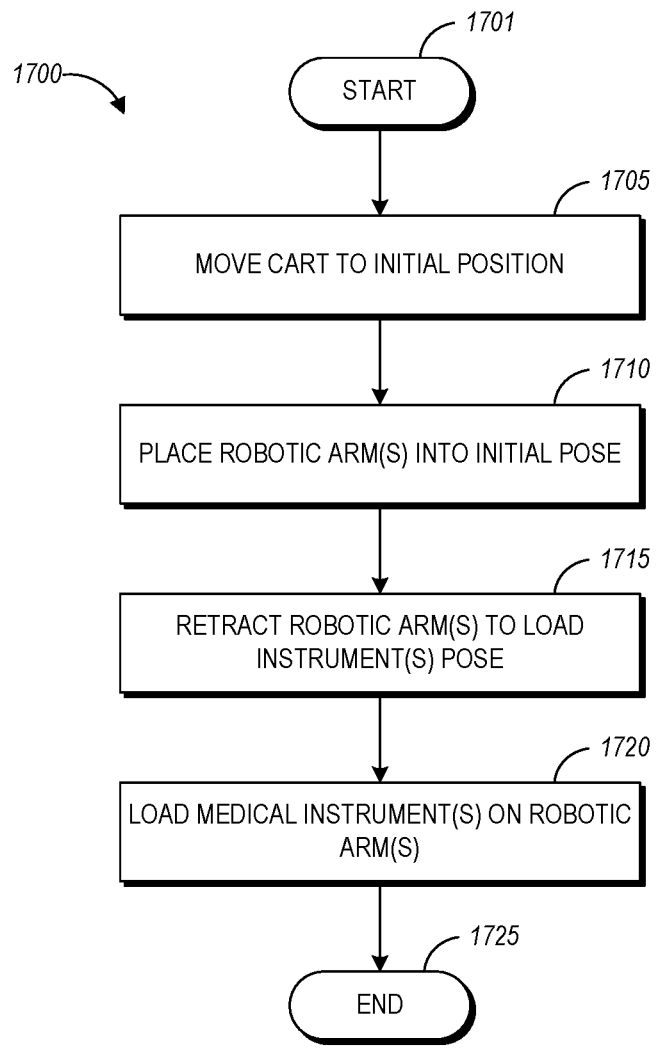
FIG. 17 is a flowchart illustrating features of an example setup procedure for a bronchoscopy procedure in accordance with aspects of this disclosure.

FIG. 17 is a flowchart illustrating features of an example setup procedure for a bronchoscopy procedure in accordance with aspects of this disclosure. The method 1700 illustrated in FIG. 17 is merely an example implementation and the method 1700 may be modified by adding, removing, and or modifying one or more of the blocks associated with the method 1700. Although FIG. 17 uses bronchoscopy as an example medical procedure to facilitate the description of the setup procedure, aspects of this disclosure relate generally to the movement of a robotic arm through the use of forces applied thereto, and thus, may apply to other medical procedures or simply to the movement of a robotic arm.

The method 1700 begins at block 1701. At block 1705, the method 1700 involves moving the cart to an initial position. For example, a user may move the cart to be positioned proximate to (e.g., within a defined distance of) the patient's access point. Once the cart has been moved into position, the user may immobilize the cart by, for example, locking the casters of the cart. Block 1710 may involve an arm setup phase, in which the user may place one or more of the robotic arms into an initial pose.

In certain medical procedures, the robotic arm(s) 112 may need to be aligned with the patient prior to performing the procedure. Thus, the arm setup phase may include an alignment step for aligning one or more of the robotic arms 112 with an access point of the patient. Since the access point used may depend on the type of the medical procedure being performed, the specific alignment procedure may depend on the medical procedure type. In the example of bronchoscopy, a patient introducer may be used to guide a bronchoscope into the patient's mouth. The patient introducer may be inserted into the patient's mouth and the robotic arm may be aligned with the patient by aligning the robotic arm with the patient introducer. Thus, in one implementation of a bronchoscopy setup procedure, the user may align a first one of the robotic arms with the patient introducer. The remaining robotic arm(s) may automatically align with the pose of the first robotic arm selected by the user, for example, by maintaining a virtual rail between the first robotic arm and the remaining robotic arm(s).

In certain implementations, the movement of the robotic arm may be restricted to within certain boundary (e.g., area or volume). The system may prevent the user from moving the IDM outside of the boundary by simulating a "virtual wall" at the boundary. In certain implementations, the boundary may ensure that the pose of the robotic arm when in alignment with the patient allows for a sufficient movement of the robotic arm to perform the desired medical procedure.

After the first robotic arm is aligned with the patient introducer, at block 1715, the system retracts the robotic arm(s) into a load instrument(s) pose. In some embodiments, the system may retract the robotic arm(s) into the load instrument(s) pose in response to receiving a load instrument pose input from the user. This input may indicate that the user has completed the alignment step and is ready to load the instruments (e.g., the sheath and scope of the bronchoscope) onto the robotic arms. At block 1720, the user loads the medical instruments onto the corresponding robotic arm(s). The method 1700 ends at block 1725.

C. Determination of Force Applied to Robotic Arm.

Although the positioning of the robotic arms may be controlled remotely by a user or by a surgical robotic system, the remote control of the robotic arms may not be convenient during an alignment phase in which at least one of the robotic arms is aligned with the patient. For example, during a bronchoscopy, endoscopy, or a similar procedure, one or more robotic arms may be aligned with a patient introducer, which may involve identifying the location of the patient introducer within the system's local coordinate system. Referring back to FIG. 16, the alignment procedure may involve moving the first robotic arm 110 such that the IDM 115 is in contact with the alignment member 133. The alignment member 133 may be configured to facilitate alignment with the IDM 115 by defining a specific location and orientation of IDM 115 for alignment. For example, in certain embodiments, the alignment member 133 may have a shape complementary to the shape of the IDM 115 and one or more markings that define a rotational position of the IDM 115. The IDM 115 may include corresponding marking(s) which may be matched with the markings on the patient introducer 130.

Since alignment may require precise movement and positioning of the first robotic arm 110, as well as visual confirmation of alignment of the markings and/or complementary shapes of the IDM 115 with alignment member 133, it may be advantageous for the user to be in a location where both the alignment member 133 and IDM 115 are visible. Thus, in at least one implementation, the system 100 may be configured to receive user input in the form of forces applied directly to the first robotic arm 110 by the user, while in an admittance control mode. One or more of the robotic arms (e.g., the first robotic arm 110 which may be used during alignment) may further comprise an admittance control button which may be actuated by the user to enter and/or exit an admittance control mode. For example, the admittance control button may be located on within a defined distance of the IDM 115 or on another portion of the robotic arm 110. However, in other implementations, the system 100 may be configured to receive input from the user regarding entry/exit into to the admittance mode based on an admittance control button located elsewhere in the system 100 or though some other type of input other than a button, such as via a touchscreen, pedal, etc. In addition, actuation of the admittance control button or similar input component may activate admittance control mode for one robotic arm (e.g., the first robotic arm 110) or a plurality of robotic arms (e.g., the robotic arms 110 and 120).

Certain surgical robotic systems may incorporate a force sensor in each of the robotic arms to measure the force experienced at a reference point on the corresponding robotic arm. In one example, the reference point may be located on an IDM, such as IDM 115. For example, a force sensor may be positioned on or near (e.g., within a defined distance of) the IDM 115 of the first robotic arm 110 of FIG. 16 to measure the forces applied to the IDM 115. However, force sensors that are able to measure the applied force with sufficient accuracy may be costly. Thus, in certain implementations, the system may determine the force at the IDM 115 (or any reference point on the robotic arm 110) using torque values output from the torque sensors.

Figure 18:
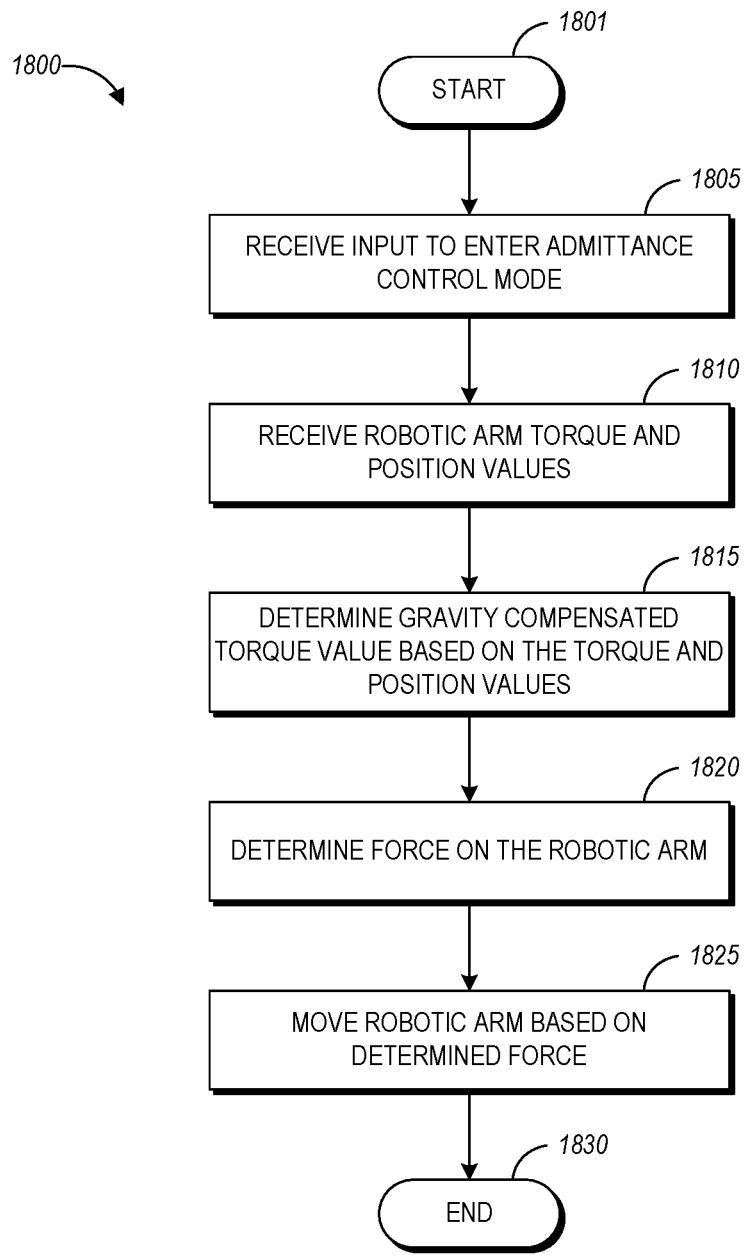
FIG. 18 is a flowchart illustrating an example procedure for determining a force applied to a robotic arm and moving a robotic arm based on the determined force in accordance with aspects of this disclosure.

FIG. 18 is a flowchart which illustrates an example procedure for determining a force applied to a robotic arm and moving a robotic arm based on the determined force in admittance mode, in accordance with aspects of this disclosure. The method 1800 illustrated in FIG. 18 is merely an example implementation and the method 1800 may be modified by adding, removing, and or modifying one or more of the blocks associated with the method 1800. For convenience, method 1800 will be described as being performed by a system (e.g., the surgical robotic system 100 of FIG. 16). However, certain aspects of the method 1800 may be performed, for example, by one or more processors of the system based on computer-executable instructions stored in memory. Further, the method 1800 will be described in connection with a single robotic arm. However, a similar method may be performed to determine the force experienced by each of the robotic arms included in the system in admittance mode.

The method 1800 begins at block 1801. At block 1805, the system receives an input from a user to enter admittance control mode. For example, the system may receive a user input signal generated when the button is actuated by the user. In one implementation, the robotic arm may comprise an admittance button that, when actuated, transitions the system into admittance control mode. At block 1810, the system receives robotic arm torque and position values. The system may receive torque values from each of the torque sensors included in the robotic arm. Further, the system may retrieve position values from position data stored in memory that indicates the position of each of the linkages in the robotic arm. For example, the robotic arms may further include a position sensor, such as an encoder formed on each of the joints. The encoder may be configured to measure the speed and/or position of the motor shaft by reading coded visual information printed on the motor shaft and may provide feedback to the system representative of the speed and/or position of the motor. The system may be configured to determine the position of each of the joints based on the feedback from the encoders. Using the information from each of the encoders positions on the robotic arm, the system can determine to position of each of the linkages and the IDM.

At block 1815, the system determines a gravity-compensated torque value for each of the joints based on the torque values and position values. The gravity-compensated torque value for a given joint may represent the component of the torque at the joint that is due to forces other than the force of gravity. In one implementation, the system may measure a first torque value at a joint based on the output of the corresponding torque sensor. The system may then determine a second torque value at the joint based on the position of the robotic arm. The position data of the robotic arm may include data that enables the system to determine the position of the two linkages connected by the joint and the angle formed therebetween. The second torque value may be indicative of a gravitational component of the torque between the two linkages. The system may then be able to determine the gravity-compensated torque value based on the first and second torque values. For example, the difference between the first and second torque values may correspond to the gravity-compensated torque value.

For example, at block 1820, the system may determine the force exerted on the robotic arm at a reference point on the robotic arm based on the gravity-compensated torque values for each of the joints. That is, the system may determine the force at the reference point based a difference between the first and second torque values. The determined force may therefore exclude the component of the forces experienced by the robotic arm due to gravity. At block 1825, the system may move the robotic arm based on the determined force at the reference point. For example, the system may determine a direction of movement of the reference point based on a position of the robotic arm and determine that a component of the force is in the same direction as the direction of movement of the reference point. The system may generate, based on the determination that the component of the force is in the same direction as the direction of movement of the reference point, at least one parameter indicative of a target resistance to movement of the robotic arm, and control at least one motor in the robotic arm, based on the at least one parameter, to move the robotic arm in accordance with the target resistance. Additional techniques for using the determined force as an input for the movement of the robotic arm will be described in greater detail below. The method 1800 ends at block 1830.

D. Robotic Arm Free-Body Diagram and Admittance Control Mode.

Figure 19:
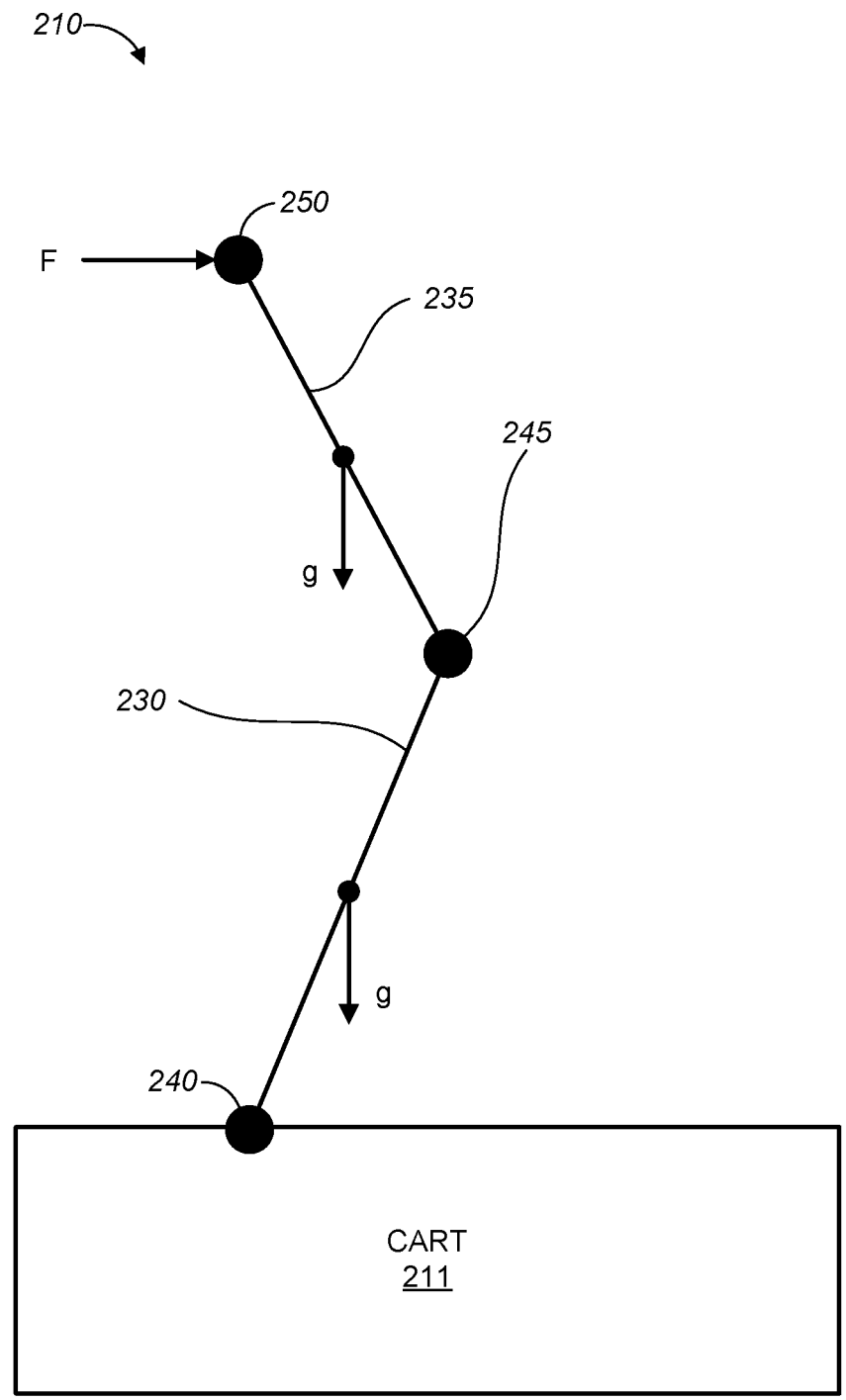
FIG. 19 is a free-body diagram of a robotic arm illustrating techniques for calculating forces applied to the robotic arm in accordance with aspects of this disclosure.

FIG. 19 illustrates a free-body diagram of a robotic arm for describing techniques for calculating forces applied to the robotic arm in accordance with aspects of this disclosure. The robotic arm 210 may be attached to a cart 211. The robotic arm 210 may include a first linkage 230, a first joint 240 connecting the first linkage to the cart 211, a second linkage 235, a second joint 245 connecting the first and second linkages 230 and 235, and an IDM 250 connected to the distal end of the second linkage 235. The robotic arm 210 is illustrated in a simplified form in FIG. 19; however, more complex robotic arms may be analyzed in a similar manner by adding additional linkages to the arm connected by additional joints. The IDM 250 may define a reference point at which an external force F is modeled as being applied to the robotic arm 210. However, in other embodiments, the reference point may be set to any other point along the robotic arm 210. Additionally, the force due to gravity experienced by each of the first and second linkages 230 and 235 is illustrated in the diagram as a gravity force vector g applied at the center of gravity of the corresponding linkage 230 and 235.

Figure 20:
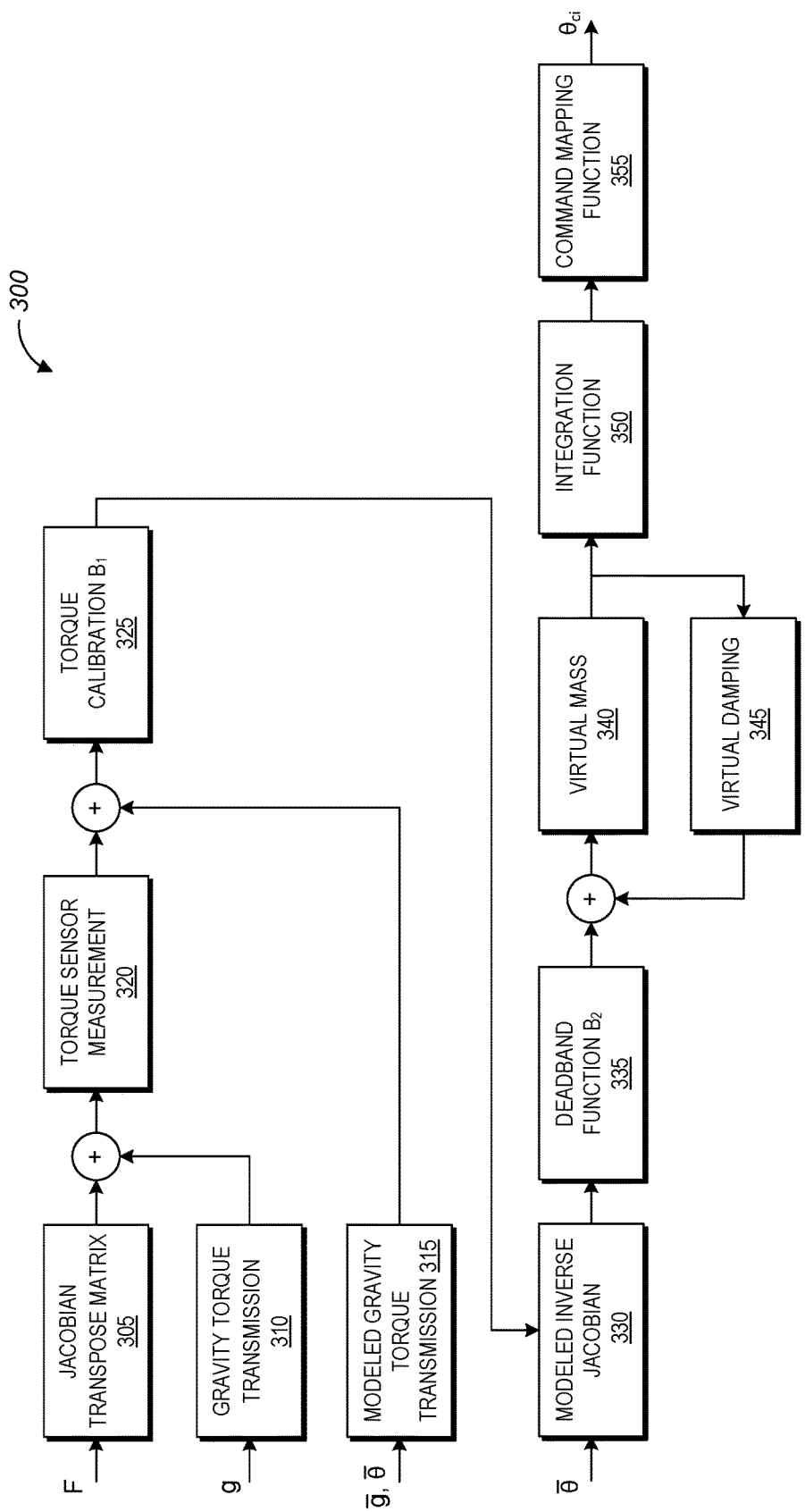
FIG. 20 is a block diagram illustrating an example procedure for using a force detected at a reference point on a robotic arm as an input for controlling movement of the robotic arm in accordance with aspects of this disclosure.

FIG. 20 is a block diagram illustrating an example procedure for using a force detected at a reference point on a robotic arm as an input for controlling movement of the robotic arm in accordance with aspects of this disclosure. The procedure 300 may be operable by a surgical robotic system or component(s) thereof. The procedure 300 illustrated in FIG. 20 may involve receiving a number of inputs including a force F applied to the robotic arm, the force due to gravity g applied to the robotic arm, a modeled force due to gravity $\bar{g}$ applied to the robotic arm, an indication of the joint positions $\bar{\theta}$ of the robotic arm. In certain embodiments, the system may further include a joint controller, which may be implemented via separate hardware or with the processor, configured to move the robotic arm using command information $\theta_{ci}$. The technique 300 may involve outputting command information $\theta_{ci}$ which may be used by the joint controller to instruct motor(s) in the robotic arm to move the robotic arm into a new pose. As discussed below, the joint controller may receive the command information $\theta_{ci}$ and generate the indication of the joint positions $\bar{\theta}$ of the robotic arm, which may be fed back as an input to the technique 300.

For example, with reference to FIG. 19, each of the joints 240 and 245 may include a torque sensor configured to output a measured torque value $\tau_{measured}$. The measured torque value $\tau_{measured}$ at each of the joints 240 and 245 may be determined according to the following equation:

$$\tau_{measured} = \tau_{force} + \tau_{gravity} \tag{1}$$

where $\tau_{measured}$ is the measured torque value, $\tau_{force}$ is the torque at the joint 240 or 245 due to the force F applied to the robotic arm 210, and $\tau_{gravity}$ is the torque applied to joint 240 or 245 due to the force of gravity g. In this embodiment, the force F applied to the robotic arm 210 is modelled as being applied to the IDM 250 as a reference point. However, the force may be modelled as being applied to the robotic arm 210 at difference points depending on the embodiment.

The torque due to the force F applied at the reference point and the torque due to gravity g may be determined as follows:

$$\tau_{force} = J(\theta)^T F \tag{2}$$

$$\tau_{gravity} = G(\theta, g) \tag{3}$$

where $J(\theta)^T$ is a Jacobian transpose matrix that represents the transmission of the force F to the joint 240 or 245 based on the positions of the joints 240 or 245 in the robotic arm 210 and $G(\theta, g)$ represents the transmission of torque to the joints 240 or 245 due to gravity g. $\theta$ represents the angular positions of each of the joints in the robotic arm (e.g., the position of the robotic arm). Substituting equations (2) and (3) into (1) gives:

$$\tau_{measured} = (\theta)^T F + G(\theta, g) \tag{4}$$

Accordingly, the force F applied to the reference point (e.g., the IDM 250) can be solved based on the measured torques $\tau_{measured}$, the Jacobian transpose matrix $J(\theta)^T$, and the transmission of torque due to gravity $G(\theta, g)$.

Equation (4) may be visualized as shown in FIG. 20, where the torque sensor measurement block 320 can be determined based on the sum of the output of the Jacobian transpose matrix block 305 (e.g., $J(\theta)^T F$) and the gravity torque transmission block 310 (e.g., $G(\theta, g)$). The Jacobian transpose matrix block 305 takes the force F as an input while the gravity torque transmission block 310 takes the value of gravity gas an input.

In certain embodiments, the torque due to gravity $G(\theta,g)$ is modeled as a modeled torque due to gravity $\overline{G}(\overline{\theta},\overline{g})$. This is shown as the modeled gravity torque transmission block 315 in FIG. 20 which takes the modeled force of gravity $\overline{g}$ and the modeled joint position $\overline{\theta}$ as inputs. There may be a certain amount of uncertainty in the modeled torque due to gravity $\overline{G}(\overline{\theta},\overline{g})$ as shown in the following equation:

$$G(\theta,g)-\overline{G}(\overline{\theta},\overline{g})=\Delta G(\theta,g,\overline{\theta},\overline{g})\neq 0. \quad (5)$$

In certain implementations, the force of gravity g is approximately equal to the modeled force of gravity $\overline{g}$ and the modeled joint position $\overline{\theta}$ may be defined as equal to $\theta+n$, where n is a value representative of the uncertainty in the joint position sensor measurements. The uncertainty in the joint position sensor measurements n may reflect the noise or uncertainty in the measurement from each of the sensors contributing to the joint position measurements (e.g., the position sensors). Accordingly, equation (5) may be simplified as follows:

$$\Delta G(\theta,g,\overline{\theta},\overline{g})=\Delta G(\theta,g,n) \quad (6)$$

Thus, the uncertainty in the modeled torque due to gravity $\Delta G$ may be a function of the force of gravity g, the angular positions of each of the joints in the robotic arm $\theta$, and the value representative of the uncertainty in the joint position sensor measurements n.

The system may determine a value $\tau$ as the torque experienced at the reference point due to the force, perturbed by the modeled torque due to gravity $\Delta G$:

$$\tau=\tau_{measured}-\overline{G}(\overline{\theta},\overline{g})=J(\theta)^T F+G(\theta,g)-\overline{G}(\overline{\theta},\overline{g})=J(\theta)^T F+\Delta G(\theta,g,n) \quad (7)$$

In certain implementations, the output of the torque sensors may be noisy and may drift over time. In order to address the drifting error in the output of the torque sensors, the system may perform a calibration by adjusting the output of the torque sensor to zero when the robotic arm is stationary (e.g., there are no non-gravity forces acting on the robotic arm). In one embodiment, the system may calibrate the torque sensor based on the output received from the torque sensor(s) over a period of time. For example, for each joint in the robotic arm while the robotic arm is stationary, the system may average the measure torque value $\tau_{measured}$ over a certain period of time (e.g., over 1 s), determine a gravity-compensated torque for the current pose of the arm, and set the adjust the output values for the gravity-compensated torque to zero. In certain implementations, the system may perform this calibration of the torques sensors each time the admittance button is actuated. However, in other implementations, the system may calibrate the torque sensors at another interval. Accordingly, the system may determine the force at the reference point in response to receiving the user input signal (e.g., the actuation of the admittance button) and based on the calibrated output from the torque sensor(s).

The torque sensor calibration may be represented by a function $B_1$ as follows:

$$\tau'=B_1(\tau) \quad (8)$$

Returning to FIG. 20, the torque calibration $B_1$ block 325 is applied to the outputs of the torque sensor measurement block 320 and the modeled gravity torque transmission block 315, consistent with equation (8).

In certain embodiments, as previously discussed, the robotic arm may not include a dedicated force sensor at the reference point. Accordingly, the system may determine the apparent reference point force according to the following equation:

$$\overline{F}=\overline{J}(\overline{\theta})^{-T}\tau' \quad (9)$$

where $\overline{J}$ is a model of the Jacobian which is a function of the measured joint position $\overline{\theta}$. As shown in equation (9) and FIG. 20, the modeled inverse Jacobian block 330 is applied to the calibrated torque sensor output (e.g., the output of torque calibration $B_1$ block 325) using the measured joint position $\overline{\theta}$ as a second input.

Figure 21:
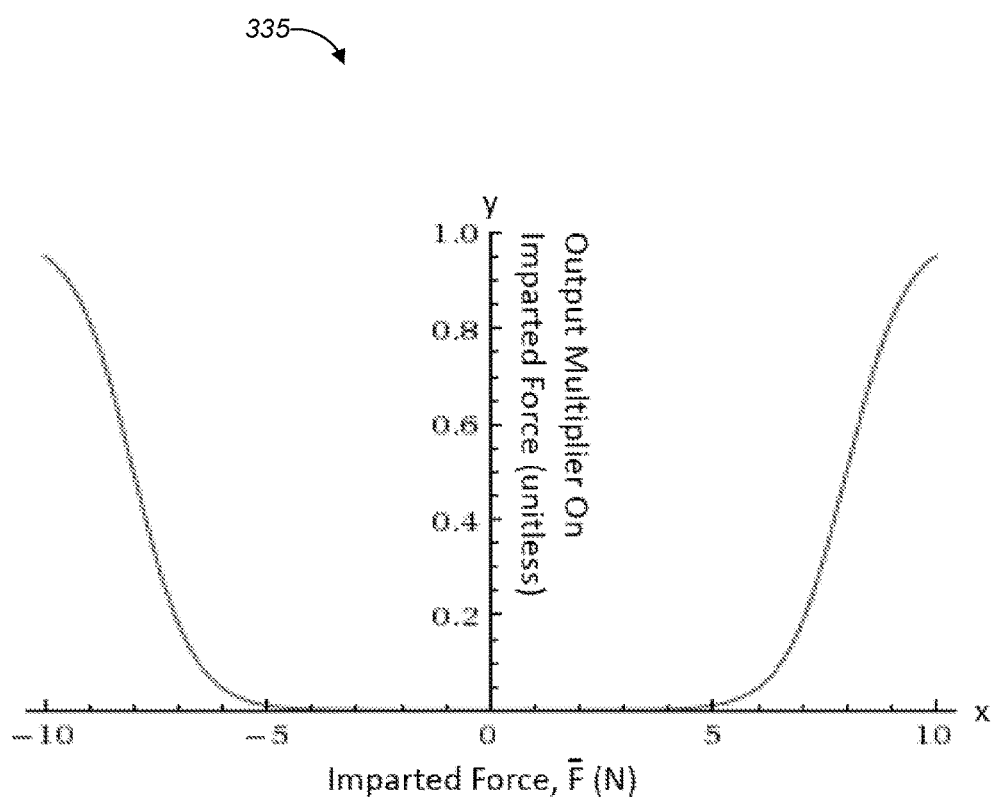
FIG. 21 is a graph illustrating an example of a deadband function which may be applied to a measured reference point force in accordance with aspects of this disclosure.

The system may also apply a deadband to the apparent reference point force $\overline{F}$. In certain embodiments, the deadband may restrict movement of the robotic arm to be response to only values of the force outside of the deadband. The deadband may improve the user's experience in controlling movement of the robotic arm by preventing small, potentially inadvertent forces on the robotic arm or IDM from causing movement in the robotic arm. The deadband may also function to remove any noise in the torque sensor output from effecting movement of the robotic arm. The transitions in the deadband may also be smoothed to prevent the robotic arm from exhibiting "jumps" in movement (e.g., accelerating to a high movement speed very quickly) in response to force(s) imparted to the robotic arm by the user or noise in the torque sensor output. Such implementations may facilitate a more controlled, fine motion of the robotic arms. In one implementation, the deadband may be formed by a range of ±4 N with smoothed edges by apply a smoothing function to the force values at boundaries of the deadband. Thus, the system may further control movement of the robotic arm based on the smoothed force values. For example, the following functions $B_2$ may be used as a unitless multiplier to the apparent reference point force $\overline{F}$ to provide a deadband with smoothed edges:

$$\overline{F}' = B_2(\overline{F})\overline{F} \quad (10)$$

$$B_2(x) = y = \frac{1}{e^{-1.5(|x|-8)} + 1} \quad (11)$$

where the value 1.5 is an adjustable parameter that adjusts the transitions in the edge of the deadband (e.g., defining the "smoothness" of the transition), x is the imparted force input value, and the value 8 is an adjustable parameter that defines the width of the deadband. The application of the deadband is illustrated by deadband function $B_2$ block 335. FIG. 21 is a graph illustrating an example of a deadband function which may be applied to a measured reference point force in accordance with aspects of this disclosure. Specifically, the deadband function illustrated in FIG. 21 illustrates the values of the unitless multiplier y in equation (11) for values of x ranging from −10 to 10.

The system may control the movement of the robotic arm based on the apparent reference point force $\overline{F}'$ applied with the deadband using a virtual model of the robotic arm. Depending on the embodiment, the system may determine a target resistance to movement of the robotic arm for use in the virtual model. The target resistance to movement may include, for example, a first parameter defining a virtual mass of the robotic arm, and a second parameter defining a virtual damping coefficient of the robotic arm. Thus, the system may control the motor to move the robotic arm based on a model of the robotic arm, the model defining a relationship between the control of the motor, the force at the reference point, the first parameter, and the second parameter.

The system may also update the target resistance based on a direction of movement of the robotic arm. In one embodiment, the system may determine a direction of movement of the reference point of the robotic arm based on the joint position of the robotic arm θ. In other embodiments, the direction of movement may be determined based on the Cartesian position of the robotic arm X(s), as shown below.

The system may further determine whether a component of the direction of the force (e.g., the post-deadband apparent reference point force F') is in the same direction as the direction of movement of the reference point. The system may adjust the target resistance to movement (e.g., one or more of the first and second parameters) based on whether the component of the direction of the post-deadband apparent reference point force F' is in the same direction as the direction of movement of the reference point. In one example, the system may decrease the first and second parameters in response to determining that the component of the force is in the same direction as the direction of movement of the reference point. The system may also determine that the component of the force is in an opposite direction from the direction of movement of the reference point, and increase the first and second parameters in response to determining that the component of the force is in the opposite direction from the direction of movement of the reference point.

By adjusting the first and second parameters based on the comparison of the direction of the force to the direction of movement of the robotic arm, the system may infer the intent of the user in imparting force to the robotic arm. That is, when the user is applying a force having a component in the direction of the movement of the robotic arm, the user intent may be to accelerate movement of the robotic arm in the direction of the force. Similarly, when the user is applying a force having a component in a direction opposite to the direction of the movement of the robotic arm, the user intent may be to decelerate movement of the robotic arm in the direction of the force. Accordingly, the system may be configured to control the movement of the robotic arm in a manner that is consistent with the intent of the user.

Referring again to FIG. 20, the virtual mass block 240 and the virtual damping block 345 may be applied to the output of the deadband function $B_2$ block 335 (e.g., post-deadband apparent reference point force F'). This may result in a virtual model of the robotic arm that provides improved feedback to the user.

In one implementation, the virtual model may be expressed as:

$$\dot{X}(s) = [I + \overline{M}(s)\overline{D}]^{-1}\overline{M}(s)\overline{F}'(s) \text{ where:} \quad (12)$$

$$\overline{M}(s) = \begin{bmatrix} 1/m_{11}s & \cdots & 0 \\ \vdots & \ddots & \vdots \\ 0 & \cdots & 1/m_{66}s \end{bmatrix}, \quad (13)$$

$$\overline{D} = \begin{bmatrix} d_{11} & \cdots & 0 \\ \vdots & \ddots & \vdots \\ 0 & \cdots & d_{66} \end{bmatrix} \text{ and}$$

$$I = \begin{bmatrix} 1 & \cdots & 0 \\ \vdots & \ddots & \vdots \\ 0 & \cdots & 1 \end{bmatrix}$$

Here, s is a Laplace variable and $\dot{X}(s)$ is the Cartesian velocity of the robotic arm. $\overline{M}(s)$ and $\overline{D}$ are mass and damping matrices which may be specified at the robotic arm level. The mass and damping parameters may be selected to define the feel of the motion of the robotic arm which the user experiences. In certain embodiments, matrices $\overline{M}(s)$ and $\overline{D}$ are diagonal, which may allow for a single mass parameter and a single damping parameter to be selected to define the feel of the robotic arm movement in each Cartesian direction and orientation as follows:

$$[I + \overline{M}(s)\overline{D}]^{-1}\overline{M}(s) = \begin{bmatrix} 1/(m_{11}s + d_{11}) & \cdots & 0 \\ \vdots & \ddots & \vdots \\ 0 & \cdots & 1/(m_{66}s + d_{66}) \end{bmatrix} \quad (14)$$

In certain implementations, the system may store a plurality of user profiles in memory. Each of the user profiles may define values for the first and second parameters. For example, certain users may have preferences for the configuration of the first and second parameters that matches a desired response of the movement of the robotic arm to the force applied thereto. Accordingly, the system may be further configured to receive a selection of one of the user profiles and adjust the first and second parameters based on the received selection. For example, prior to entering admittance mode, the user may provide an input to a touchscreen of the system indicative of a selected user profile and the system may configured the first and second parameters based on the selected user profile to provide the user with the selected movement response profile.

In order to determine the position of the robotic arm X(s), the system may integrate, at integration function block 350, the velocity of the robotic arm $\dot{X}(s)$ as shown below:

$$X(s) = \begin{bmatrix} 1/s & \cdots & 0 \\ \vdots & \ddots & \vdots \\ 0 & \cdots & 1/s \end{bmatrix} \dot{X}(s) \quad (15)$$

The position information X(s) for the robotic arm may be used to determine command information $\theta_{ci}$, which may be determined at command mapping function block 355, used to adjust the joint position θ as follows:

$$\theta_{ci} = \overline{IK}(X) \quad (16)$$

where $\overline{IK}$ is a command mapping function which maps the position information X(s) for the robotic arm determined based on the post-deadband apparent reference point force F', to the command information $\theta_{ci}$. Thus, as shown in equations (1)-(16), the system may determine the joint position command information $\theta_{ci}$ based on the at least one parameter and the force.

The joint controller may transmit the joint position command information to the motor(s) of the robotic arm. In providing instructions for moving the robotic arm, the joint controller may determine a value for the indication of the joint positions $\overline{\theta}$ of the robotic arm which may be provided as feedback to blocks 315 and 330. The system may further be configured to determine the indication of the direction of movement of the reference point based on the command information. For example, using current and previous samples of the value for the indication of the joint positions $\overline{\theta}$, the system may determine the direction in which the reference point on the robotic arm is moving.

Based on the technique 300 described above, the system may provide an intuitive admittance control mode for a user. For example, after application of the deadband function $B_2$ block 335 and the virtual mass and damping blocks 340 and 345, the system may provide command information for movement of a robotic arm in which the movement of the robotic arm is proportional to the applied force when the force is outside of the deadband region. Further, by applying the deadband to the force, unintended forces applied to the robotic arm are prevented from actuating movement, improving the sense of control by the user. Proper application of the deadband thresholds still enable the robotic arm to be moved with relatively low forces imparted by the user.

In certain implementations, the system may further be configured to stop all motion when the detected force exerted on the robotic arm by the user goes to zero. That is, if the user releases the robotic arm, the system may slow the movement to a stop at a predetermined rate. In one embodiment, the system may detect that the force exerted on the robotic arm is less than a threshold force for a time period that is greater than a threshold period. In response to detecting that the force exerted on the robotic arm is less than the threshold force for a time period that is greater than the threshold period, the system may apply a breaking force to the motors of the robotic arm to stop further movement of the robotic arm.

E. Example Admittance Control Technique.

Figure 22:
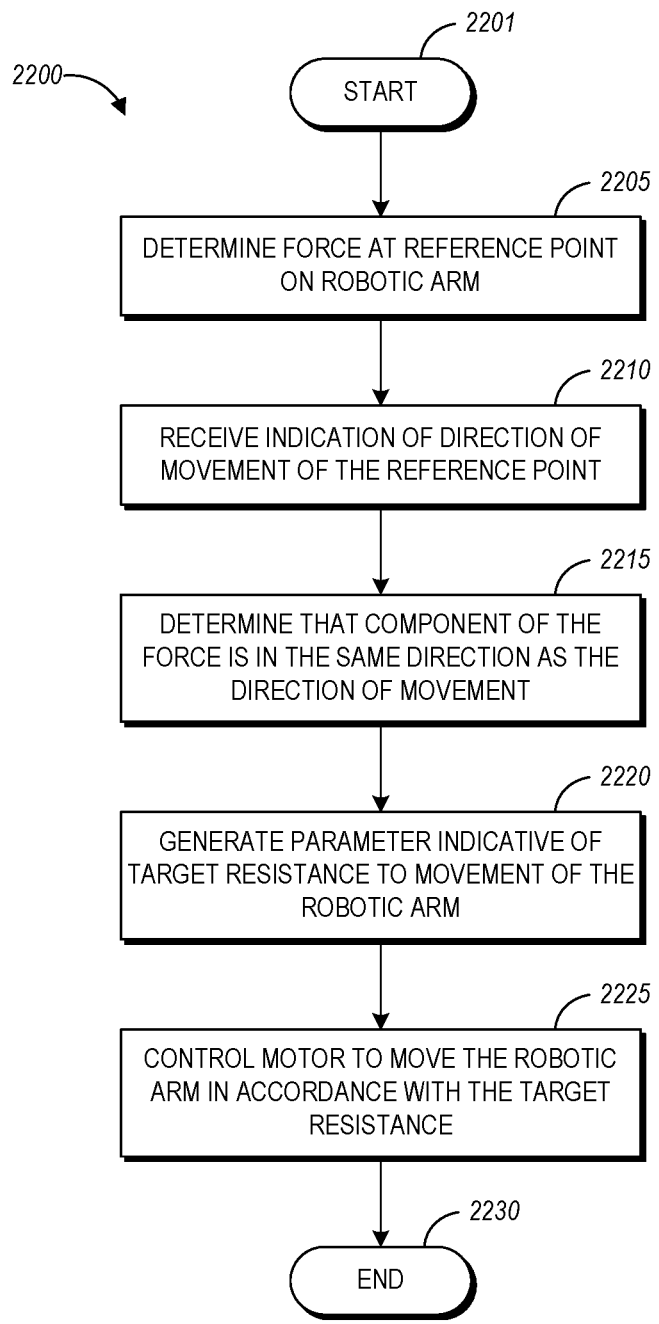
FIG. 22 is a flowchart illustrating an example admittance control method operable by a surgical robotic system, or component(s) thereof, in accordance with aspects of this disclosure.

In one example implementation, the surgical robotic system may be configured to detect a force applied to a robotic arm and use the detected force as an input for movement of the robotic arm in an admittance control mode. FIG. 22 is a flowchart illustrating an example method operable by a surgical robotic system, or component(s) thereof, for an admittance control mode in accordance with aspects of this disclosure. For example, the steps of method 2200 illustrated in FIG. 22 may be performed by a processor of a surgical robotic system. For convenience, the method 2200 is described as performed by the processor of the system.

The method 2200 begins at block 2201. At block 2205, the processor determines a force at a reference point on a robotic arm based on an output of at least one torque sensor. The robotic arm may include: at least two linkages, at least one joint connecting the at least two linkages, the at least one torque sensor configured to detect torque between the at least two linkages, and at least one motor configured to adjust the position of the at least two linkages. In certain embodiments, the processor may also determine the force based on an output of the position sensor. In these embodiments, the position sensor may be configured to measure an angle between the two adjacent linkages.

At block 2210, the processor receives an indication of a direction of movement of the reference point. At block 2215, the processor determines that a component of the force is in the same direction as the direction of movement of the reference point. At block 2220, the processor generates, based on the determination that the component of the force is in the same direction as the direction of movement of the reference point, at least one parameter indicative of a target resistance to movement of the robotic arm. At block 2225, the processor controls the motor, based on the at least one parameter, to move the robotic arm in accordance with the target resistance. The method 2200 ends at block 2230.

3. Implementing Systems and Terminology

Implementations disclosed herein provide systems, methods and apparatus for surgical robotic arm admittance control. This control mode may include, in certain embodiments, determining a force applied to a reference point of the robotic arm and controlling movement of the robotic arm using the determined force as in input.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The techniques for admittance control mode described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method of driving movement of a robotic arm, comprising:
   receiving an indication of a direction of movement of a reference point on a robotic arm, the robotic arm comprising at least two linkages, at least one joint connecting the at least two linkages, and at least one sensor configured to output data indicative of a force at the reference point;
   determining a direction of the force at the reference point based on the data received from the at least one sensor,
   determining an intent of a user manually moving the robotic arm based on a comparison of the direction of movement of the reference point and the direction of the force at the reference point; and
   driving movement of the robotic arm based on the determined intent.

2. The method of claim 1, wherein:
   the robotic arm further comprises at least one motor configured to adjust the position of the at least two linkages, and
   the driving of the movement of the robotic arm comprises controlling the at least one motor to move the robotic arm in accordance with the determined intent.

3. The method of claim 1, wherein determining the intent of the user comprises:
   determining that a component of the force at the reference point is in the same direction as the direction of movement of the reference point, and
   determining that the intent of the user is to accelerate movement of the robotic arm in response to determining that the component of the force at the reference point is in the same direction as the direction of movement of the reference point.

4. The method of claim 1, wherein determining the intent of the user comprises:
   determining that a component of the force at the reference point is in the opposite direction as the direction of movement of the reference point, and
   determining that the intent of the user is to decelerate movement of the robotic arm in response to determining that the component of the force at the reference point is in the opposite direction as the direction of movement of the reference point.

5. The method of claim 1, wherein the at least one sensor comprises a torque sensor configured to detect torque between the at least two linkages of the robotic arm.

6. The method of claim 5, further comprising:
   determining the force at the reference point on the robotic arm based on an output of the torque sensor.

7. The method of claim 5, further comprising:
   measuring a first torque value at the at least one joint based on an output of the torque sensor;
   determining a second torque value at the at least one joint based on a position of the robotic arm, the second torque value indicative of a gravitational component of the torque between the at least two linkages; and
   determining the force at the reference point based on a difference between the first and second torque values.

8. The method of claim 1, wherein:
   the robotic arm further comprises an instrument device manipulator (IDM) connected to a distal end of the robotic arm, and
   the reference point is located on the IDM.

9. The method of claim 1, wherein:
   the memory further comprises computer-executable instructions to cause the processor to determine a deadband of the force, and
   the driving of the movement of the robotic arm is further based on restricting movement of the robotic arm to be responsive to values of the force outside of the deadband.

10. The method of claim 1, wherein driving movement of the robotic arm comprises:
    determining a first parameter defining a virtual mass of the robotic arm with respect to movement of the robotic arm, and
    determining a second parameter value defining a virtual damping coefficient of the robotic arm with respect to movement of the robotic arm,
    wherein the driving of the movement of the robotic arm is further based on the first parameter and the second parameter.

11. A non-transitory computer readable storage medium having stored thereon instructions that, when executed, cause at least one computing device to:
    receive an indication of a direction of movement of a reference point on a robotic arm, the robotic arm comprising at least two linkages, at least one joint connecting the at least two linkages, and at least one sensor configured to output data indicative of a force at the reference point,
    determine a direction of the force at the reference point based on the data received from the at least one sensor,
    determine an intent of a user manually moving the robotic arm based on a comparison of the direction of movement of the reference point and the direction of the force at the reference point, and
    drive movement of the robotic arm based on the determined intent.

12. The non-transitory computer readable storage medium of claim 11, wherein:
    the robotic arm further comprises at least one motor configured to adjust the position of the at least two linkages, and
    the driving of the movement of the robotic arm comprises controlling the at least one motor to move the robotic arm in accordance with the determined intent.

13. The non-transitory computer readable storage medium of claim 11, wherein the instructions that cause at least one computing device to determine the intent of the user further cause the at least one computing device to:
    determine that a component of the force at the reference point is in the same direction as the direction of movement of the reference point, and
    determine that the intent of the user is to accelerate movement of the robotic arm in response to determining that the component of the force at the reference point is in the same direction as the direction of movement of the reference point.

14. The non-transitory computer readable storage medium of claim 11, wherein the instructions that cause at least one computing device to determine the intent of the user further cause the at least one computing device to:
    determine that a component of the force at the reference point is in the opposite direction as the direction of movement of the reference point, and
    determine that the intent of the user is to decelerate movement of the robotic arm in response to determining that the component of the force at the reference point is in the opposite direction as the direction of movement of the reference point.

15. The non-transitory computer readable storage medium of claim 11, wherein the at least one sensor comprises a torque sensor configured to detect torque between the at least two linkages of the robotic arm.

16. The non-transitory computer readable storage medium of claim 15, further having stored thereon instructions that, when executed, cause at least one computing device to:
determine the force at the reference point on the robotic arm based on an output of the torque sensor.

17. The non-transitory computer readable storage medium of claim 15, further having stored thereon instructions that, when executed, cause at least one computing device to:
measure a first torque value at the at least one joint based on an output of the torque sensor;
determine a second torque value at the at least one joint based on a position of the robotic arm, the second torque value indicative of a gravitational component of the torque between the at least two linkages; and
determine the force at the reference point based on a difference between the first and second torque values.

18. The non-transitory computer readable storage medium of claim 11, wherein:
the robotic arm further comprises an instrument device manipulator (IDM) connected to a distal end of the robotic arm, and
the reference point is located on the IDM.

19. The non-transitory computer readable storage medium of claim 11, wherein:
the non-transitory computer readable medium further has stored thereon instructions that, when executed, cause at least one computing device to determine a deadband of the force, and
the driving of the movement of the robotic arm is further based on restricting movement of the robotic arm to be responsive to values of the force outside of the deadband.

20. The non-transitory computer readable storage medium of claim 11, wherein the instructions that cause at least one computing device to drive movement of the robotic arm further cause the at least one computing device to:
determine a first parameter defining a virtual mass of the robotic arm with respect to movement of the robotic arm, and
determine a second parameter value defining a virtual damping coefficient of the robotic arm with respect to movement of the robotic arm,
wherein the driving of the movement of the robotic arm is further based on the first parameter and the second parameter.

21. A system, comprising:
a robotic arm comprising:
at least two linkages,
at least one joint connecting the at least two linkages, and
at least one sensor configured to output data indicative of a force at a reference point on the robotic arm;
a processor; and
a memory storing computer-executable instructions to cause the processor to:
receive an indication of a direction of movement of the reference point,
determine a direction of the force at the reference point based on the data received from the at least one sensor,
determine an intent of a user manually moving the robotic arm based on a comparison of the direction of movement of the reference point and the direction of the force at the reference point, and
drive movement of the robotic arm based on the determined intent.

22. The system of claim 21, wherein:
the robotic arm further comprises at least one motor configured to adjust the position of the at least two linkages, and
the driving of the movement of the robotic arm is based on controlling the at least one motor to move the robotic arm in accordance with the determined intent.

23. The system of claim 21, wherein the computer-executable instructions that cause the processor to determine the intent of the user further cause the processor to:
determine that a component of the force at the reference point is in the same direction as the direction of movement of the reference point, and
determine that the intent of the user is to accelerate movement of the robotic arm in response to determining that the component of the force at the reference point is in the same direction as the direction of movement of the reference point.

24. The system of claim 21, wherein the computer-executable instructions that cause the processor to determine the intent of the user further cause the processor to:
determine that a component of the force at the reference point is in the opposite direction as the direction of movement of the reference point, and
determine that the intent of the user is to decelerate movement of the robotic arm in response to determining that the component of the force at the reference point is in the opposite direction as the direction of movement of the reference point.

25. The system of claim 21, wherein the at least one sensor comprises a torque sensor configured to detect torque between the at least two linkages of the robotic arm.

26. The system of claim 25, wherein the memory further stores computer-executable instructions to cause the processor to:
determine the force at the reference point on the robotic arm based on an output of the torque sensor.

27. The system of claim 25, wherein the memory further stores computer-executable instructions to cause the processor to:
measure a first torque value at the at least one joint based on an output of the torque sensor,
determine a second torque value at the at least one joint based on a position of the robotic arm, the second torque value indicative of a gravitational component of the torque between the at least two linkages, and
determine the force at the reference point based on a difference between the first and second torque values.

28. The system of claim 21, wherein:
the robotic arm further comprises an instrument device manipulator (IDM) connected to a distal end of the robotic arm, and
the reference point is located on the IDM.

29. The system of claim 21, wherein:
the memory further stores computer-executable instructions to cause the processor to determine a deadband of the force, and
the driving of the movement of the robotic arm is further based on restricting movement of the robotic arm to be responsive to values of the force outside of the deadband.

30. The system of claim 21, wherein the computer-executable instructions that cause the processor to drive movement of the robotic arm further cause the processor to:

determine a first parameter defining a virtual mass of the robotic arm with respect to movement of the robotic arm, and determine a second parameter value defining a virtual damping coefficient of the robotic arm with respect to movement of the robotic arm, wherein the driving of the movement of the robotic arm is further based on the first parameter and the second parameter.

\* \* \* \* \*